(12) United States Patent
Takeuchi et al.

(10) Patent No.: US 9,541,551 B2
(45) Date of Patent: Jan. 10, 2017

(54) ANTI-GAP43 ANTIBODY

(71) Applicant: Niigata University, Niigata-shi, Niigata (JP)

(72) Inventors: Kosei Takeuchi, Nagakute (JP); Michihiro Igarashi, Niigata (JP); Motohiro Nozumi, Niigata (JP); Asami Kawasaki, Niigata (JP)

(73) Assignee: Niigata University (JP)

( * ) Notice: Subject to any disclaimer, the term of this patent is extended or adjusted under 35 U.S.C. 154(b) by 253 days.

(21) Appl. No.: 14/352,808

(22) PCT Filed: Oct. 19, 2012

(86) PCT No.: PCT/JP2012/077163
§ 371 (c)(1),
(2) Date: Jul. 15, 2014

(87) PCT Pub. No.: WO2013/058388
PCT Pub. Date: Apr. 25, 2013

(65) Prior Publication Data
US 2015/0044700 A1  Feb. 12, 2015

(30) Foreign Application Priority Data

Oct. 20, 2011 (JP) .................. 2011-230577

(51) Int. Cl.
*G01N 33/566* (2006.01)
*C07K 16/18* (2006.01)
*C07K 16/44* (2006.01)
*G01N 33/68* (2006.01)

(52) U.S. Cl.
CPC ............ *G01N 33/566* (2013.01); *C07K 16/18* (2013.01); *C07K 16/44* (2013.01); *G01N 33/6854* (2013.01); *C07K 2317/33* (2013.01); *C07K 2317/82* (2013.01); *G01N 2440/14* (2013.01)

(58) Field of Classification Search
None
See application file for complete search history.

(56) References Cited

FOREIGN PATENT DOCUMENTS

WO  2013/058388 A1  4/2013

OTHER PUBLICATIONS

Harlow et al. (Antibodies a laboratory manual. Cold Spring Harbor, New York: Cold Spring Harbor Laboratory Press, 1989. pp. 141-157).*
Apel, et al., Phosphorylation of Neuromodulin (GAP-43) by Casein Kinase II, The Journal of Biological Chemistry, Jun. 5, 1991, pp. 10544-10551, vol. 266, No. 16.
Denny, Molecular Mechanisms, Biological Actions, and Neuropharmacology of the Growth-Associated Protein GAP-43, Current Neuropharmacology, 2006, pp. 293-304.
Dokas, et al., Regulation of In Vitro Phosphorylation of the Casein Kinase II Sites in B-50 (GAP-43), Brain Research, 1998), pp. 320-328.
Meiri, et al., Monoclonal Antibodies Show that Kinase C. Phosphorylation of GAP-43 During Axonogenesis is Both Spatially and Temporally Restricted In Vivo, The Journal of Cell Biology, Mar. 1991, pp. 991-1005, vol. 112, No. 5.
Spencer, et al., GAP-43, A Protein Associated with Axon Growth, is Phosphorylated at Three Sites in Cultured Neurons and Rat Brain, The Journal of Biological Chemistry, May 5, 1992, pp. 9059-9064, vol. 267, No. 13.

* cited by examiner

*Primary Examiner* — Jacob Cheu
(74) *Attorney, Agent, or Firm* — Banner & Witcoff, Ltd.

(57) ABSTRACT

An anti-GAP43 antibody which is capable of distinguishing a non-phosphorylated threonine residue at position 89 (T89) from a phosphorylated threonine residue at position 89 (pT89) of mouse GAP43 set forth in SEQ ID NO: 13, and which is capable of specifically detecting a growth cone; an anti-GAP43 antibody which is capable of distinguishing a non-phosphorylated serine residue at position 96 (S96) from a phosphorylated serine residue at position 96 (pS96) of mouse GAP43, and which is capable of specifically detecting a growth cone; an anti-GAP43 antibody which is capable of distinguishing a non-phosphorylated threonine residue at position 172 (T172) from a phosphorylated threonine residue at position 172 (pT172) of mouse GAP43, and which is capable of specifically detecting a growth cone; and an immunological analysis method using these anti-GAP43 antibodies.

15 Claims, 13 Drawing Sheets

1: Anti-GAP43 pS96 antibody
2: Anti-GAP43 pT172 antibody
3: Anti-GAP43 pT89 antibody
4: Anti-GAP43 pS145 antibody
5: Anti-GAP43 pT171 antibody
6: Anti-GAP43 pS142 antibody
7: Anti-GAP43 pT172 (#2) antibody 1: GCP
2: PC12D
3: COS-7
4: maxGFP
5: EGFP-GAP43 S96A
6: EGFP-GAP43 S96D
7: EGFP-GAP43 T172A
8: EGFP-GAP43 T172D

1: GCP
2: EGFP-GAP43
3: EGFP-GAP43 S96A

1: FLAG-GAP43
2: FLAG-GAP43 S96A
3: FLAG-GAP43 S96D
4: FLAG-GAP43 T172A
5: FLAG-GAP43 T172D

Anti-GAP43 monoclonal antibody

Anti-GAP43 pS96 antibody

Merged

ANTI-GAP43 ANTIBODY

RELATED APPLICATION DATA

This application is a National Stage Application under 35 U.S.C. 371 of co-pending PCT application PCT/JP2012/077163 designating the United States and filed Oct. 19, 2012; which claims the benefit of JP application number 2011-230577 and filed Oct. 20, 2011 each of which are hereby incorporated by reference in their entireties.

TECHNICAL FIELD

The present invention relates an antibody capable of specifically detecting a growth cone.

BACKGROUND ART

In neural development and regeneration, a stage (1) in which a nerve cell is developed or regenerated and a stage (2) in which an axon of the developed or regenerated nerve cell is correctly outgrown to correctly form a synapse are required. A highly motile flabellate structure called a growth cone is present at an axon tip of the developed and regenerated nerve cell. The growth cone has a central domain, and a peripheral domain including lamellipodia and filopodia. The growth cone repeats extension and retraction of its filopodia to appropriately guide an axon for synapse formation.

Growth associated protein 43 (neuromodulin) (hereinafter, referred to as "GAP43"), which is abundantly present in a growth cone, plays an important role in filopodia extension and neurite branching. GAP43 is phosphorylated by protein kinase C, and dephosphorylated by calcineurin. Non-phosphorylated GAP43, which functions as an actin capping protein, shows decreased filopodia extension. Further, phosphorylation of a serine residue at position 41 (S41) in mouse GAP43 is thought to be important to stabilize actin which is involved in filopodia extension (for example, see Denny, J B., *Curr Neuropharmacol.*, vol. 4 (12): pp. 293-304 (2006)).

Conventionally, in order to evaluate the stage (2), an anti-GAP43 antibody that recognizes phosphorylated S41 is used.

SUMMARY OF INVENTION

Technical Problem

However, the anti-GAP43 antibody reacts with GAP43 at anywhere on a whole nerve cell, and can not specifically detect a growth cone only. Therefore, the anti-GAP43 antibody can not quantitatively evaluate neural development or regeneration. Thus, there has been almost no antibody capable of specifically detecting a growth cone in the development and regeneration process.

An object of the invention is to provide an antibody capable of specifically detecting a growth cone, and an immunological analysis method using the antibody.

Solution to Problem

The inventors of the present invention have newly found, by the proteomics analysis of phosphorylation in a growth cone, that a threonine residue at position 89 (T89), a serine residue at position 96 (S96) and a threonine residue at position 172 (T172) of mouse GAP43 are significantly phosphorylated while the above S41 is not substantially phosphorylated. The findings show that phosphorylation of the above T89, S96 and T172 is important for axon outgrowth. The invention enables quantitative evaluation of neural development and/or regeneration by specifically detecting a GAP43 in which the above T89, S96 or T172 are phosphorylated.

The invention provides an anti-GAP43 antibody which is capable of distinguishing a non-phosphorylated threonine residue at position 89 (T89) from a phosphorylated threonine residue at position 89 (pT89) of mouse GAP43 set forth in SEQ ID NO: 13, and which is capable of specifically detecting a growth cone.

The invention provides an anti-GAP43 antibody which is capable of distinguishing a non-phosphorylated serine residue at position 96 (S96) from a phosphorylated serine residue at position 96 (pS96) of mouse GAP43 set forth in SEQ ID NO: 13, and which is capable of specifically detecting a growth cone.

The invention provides an anti-GAP43 antibody which is capable of distinguishing a non-phosphorylated threonine residue at position 172 (T172) from a phosphorylated threonine residue at position 172 (pT172) of mouse GAP43 set forth in SEQ ID NO: 13, and which is capable of specifically detecting a growth cone.

The invention provides an immunological analysis method for GAP43, the method including: (1) preparing at least one selected from the group consisting of the above three anti-GAP43 antibodies of the invention and a test sample, (2) contacting the anti-GAP43 antibody with the test sample, and (3) detecting or quantifying the anti-GAP43 antibody bound with the test sample.

The immunological analysis method of the invention may be used in order to evaluate neural development and/or regeneration.

In the immunological analysis method of the invention, the anti-GAP43 antibody bound with the test sample may be detected or quantified by using at least one method selected from the group consisting of the ELISA method, the western blotting method, the surface plasmon resonance method, the latex agglutination method, and the immunohistochemical method.

Each of the three anti-GAP43 antibodies of the invention may be a polyclonal antibody or a monoclonal antibody.

The invention provides a hybridoma which produces one of the above three monoclonal antibodies of the invention.

The invention provides a kit for carrying out the immunological analysis method of the invention.

The kit may include at least one anti-GAP43 antibody selected from the group consisting of the above three antibodies of the invention, and a reagent for detecting or quantifying the anti-GAP43 antibody.

The invention provides a reagent for detecting a growth cone, the reagent including at least one anti-GAP43 antibody selected from the group consisting of the above three antibodies of the invention.

The invention provides the use of at least one anti-GAP43 antibody selected from the group consisting of the above three antibodies of the invention in a method of detecting a growth cone.

The term "process" as used herein covers not only an independent process but also a process not clearly distinguishable from other processes as long as the desired effect in the process can be achieved.

Further, a range of a numerical value indicated using the word "to" as used herein shows a range in which numerical values before and after the word "to" are included as a minimum value and a maximum value, respectively.

Moreover, in the invention, in a case where each component presents as two or more substances in a composition, the amount of each component in the composition means the total amount of the two or more substances present in the composition unless otherwise stated.

When an amino acid is shown herein, the amino acid may be expressed in accordance with a compound name such as serine or threonine, or may be expressed in accordance with the conventional three-character notation such as Ser or Thr, or may be expressed in accordance with the conventional one-character notation such as S or T.

The term a "non-phosphorylated polypeptide" as used herein means a polypeptide containing only non-phosphorylated amino acid residues while the term a "phosphorylated polypeptide" as used herein means a polypeptide containing at least one phosphorylated amino acid residue.

The amino acid sequence of a polypeptide set forth in SEQ ID NO: 1 is CEGDGSATTDAAPA. The amino acid sequence of a polypeptide set forth in SEQ ID NO: 2 is CDAAPATSPKAEE. The amino acid sequence of a polypeptide set forth in SEQ ID NO: 3 is CVTDAAATTPAAED. The amino acid sequence of a polypeptide set forth in SEQ ID NO: 4 is CTDAAATTPAAED. The amino acid sequence of a polypeptide set forth in SEQ ID NO: 5 is CKATTDNSPSSKA. The amino acid sequence of a polypeptide set forth in SEQ ID NO: 6 is CTTDNSPSSKAEDG. The amino acid sequence of a polypeptide set forth in SEQ ID NO: 7 is CVTDAAATTPAAED. The amino acid sequence of a polypeptide set forth in SEQ ID NO: 8 is CKKEGDGSATTDA. The amino acid sequence of a polypeptide set forth in SEQ ID NO: 9 is CTDAAPATSPKAE. The amino acid sequence of a polypeptide set forth in SEQ ID NO: 10 is CPKAEEPSKAGDA. The amino acid sequence of a polypeptide set forth in SEQ ID NO: 11 is CSEEKAGSAETES. The amino acid sequence of a polypeptide set forth in SEQ ID NO: 12 is CTETAESSQAEEE. The amino acid sequence of GAP43 set forth in SEQ ID NO: 13 is the sequence under a GenBank accession number of AAH28288.

DESCRIPTION OF EMBODIMENTS

Figure 1:
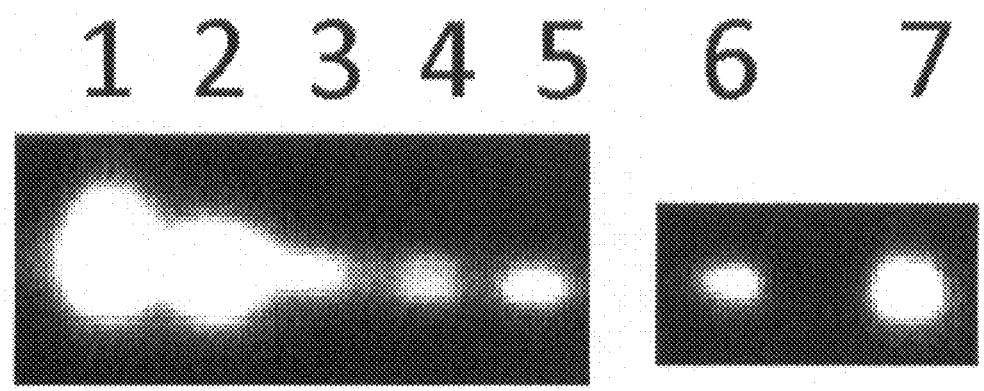
FIG. 1 shows western blot photographs illustrating results from cross reaction experiments for anti-GAP43 antibodies against a rat growth cone portion (GCP).

The antibodies of the invention are as follows:

an anti-GAP43 antibody which is capable of distinguishing a non-phosphorylated threonine residue at position 89 (T89) from a phosphorylated threonine residue at position 89 (pT89) of mouse GAP43 set forth in SEQ ID NO: 13, and which is capable of specifically detecting a growth cone, an anti-GAP43 antibody which is capable of distinguishing a non-phosphorylated serine residue at position 96 (S96) from a phosphorylated serine residue at position 96 (pS96) of mouse GAP43 set forth in SEQ ID NO: 13, and which is capable of specifically detecting a growth cone, and an anti-GAP43 antibody which is capable of distinguishing a non-phosphorylated threonine residue at position 172 (T172) from a phosphorylated threonine residue at position 172 (pT172) of mouse GAP43 set forth in SEQ ID NO: 13, and which is capable of specifically detecting a growth cone.

The invention provides an immunological analysis method for GAP43, the method including: (1) preparing at least one anti-GAP43 antibody selected from the group consisting of the three anti-GAP43 antibodies of the invention and a test sample, (2) contacting the anti-GAP43 antibody with the test sample, and (3) detecting or quantifying the anti-GAP43 antibody bound with the test sample. The kit according to the invention is indented for carrying out the immunological analysis method. That is, the kit may include at least one anti-GAP43 antibody selected from the group consisting of the above three antibodies of the invention, and may further include a reagent for detecting or quantifying the anti-GAP43 antibody. The reagent for detecting a growth cone according to the invention contains at least one anti-GAP43 antibody selected from the group consisting of the three antibodies of the invention.

In the invention, the three anti-GAP43 antibodies described above (hereinafter, they are also collectively referred to as "anti-GAP43 antibody of the invention" unless otherwise stated) are capable of specifically recognizing a GAP43 in which T86, S96, or T172 is phosphorylated. Therefore, neural development and/or regeneration can be evaluated based on the bound state of the anti-GAP43 antibody of the invention.

Hereinbelow, the invention will be described.

A polypeptide herein may be a polypeptide produced in accordance with a biological procedure. Examples of the biological procedure includes, but not limited to, a procedure in which a polynucleotide containing a nucleotide sequence encoding an amino acid sequence of the polypeptide is expressed in a non-living expression system or in an expression system where a host organism and an expression vector are used. Examples of the host organism include procaryote such as E. coli, or Bacillus subtilis, and eukaryote such as yeast, fungus, plant, or animal. An expression system in which the host organism and an expression vector are used may be a part of an organism such as a tissue or a cell, or may be a whole individual organism. Alternatively, a polypeptide herein may be a synthetic polypeptide produced in accordance with a chemical procedure in which the Fmoc method, the Boc method, or the like is used. The polypeptide is preferably used in a purified state. The amino acid sequence of the polypeptide may include a portion of the amino acid sequence of mouse GAP43. A specific serine residue or a specific threonine residue in the polypeptide may be phosphorylated.

As a complex with a career macromolecule, the above polypeptide may be used for producing the antibody of the invention and/or for implementing the immunological analysis method of the invention. The term a "career macromolecule" as used herein refers to any macromolecule which is capable of imparting immunogenicity to a hapten, and which may be a biological macromolecule such as a protein or a polysaccharide, or a synthetic macromolecule such as a polylysine. Examples of the protein used for a career macromolecule in the complex include, but not limited to bovine serum albumin, chicken ovalbumin, and keyhole-limpet hemocyanin. A complex of the career macromolecule and a polypeptide which contains an amino acid sequence of any of SEQ ID NOs: 1 to 12, and in which a specific serine residue or a specific threonine residue is phosphorylated may be formed via bonding between any functional group of the amino acids and the career macromolecule. For example, an amino group or a carboxyl group of the amino acids and any sidechain of the career macromolecule may be covalently attached through a suitable cross linking agent. Examples of the cross linking agent include, but not limited to, m-maleimidebenzoyl-N-hydroxysuccinimide ester (MBS), glutaraldehyde (GA), N-hydroxysuccinimide (NHS), and 1-ethyl-3-(3-dimethylaminopropyl)carbodiimide hydrochloride (EDC). A complex of the career macromolecule and a polypeptide which contains an amino acid sequence of any of SEQ ID NOs: 1 to 14 and in which a specific serine residue or a specific threonine residue is phosphorylated may be subjected to various protection, modification, or the like in order to enhance the immunogenicity of the phosphorylated specific serine residue or the phosphorylated specific threonine residue.

Each of the anti-GAP43 antibodies of the invention may be selected from the group consisting of a polyclonal antibody or a monoclonal antibody, an antigen binding fragment of the antibody, and a recombinant antibody or a chimeric antibody containing the antigen binding fragment.

The anti-GAP43 antibody of the invention and a hybridoma thereof may be prepared by various methods known to the person skilled in the art. For example, see Current Protocols in Immunology (Edited by John E. Coligan el al. John Wiley & Sons, Inc.).

The polypeptide or complex is to be injected as an immunogen into an animal host of any mammal (for example, mouse, rat, rabbit, sheep, or goat) or a bird (for example, chicken) in order to collect an antiserum containing the anti-GAP43 antibody of the invention. The immunogen may induce a superior immune response in a case where it is connected to the career macromolecule. The immunogen is preferably injected into the animal host in accordance with a predetermined schedule in which one or more booster immunizations are incorporated. The immunogen may be injected into the animal host after mixed with the complete or incomplete Freund's adjuvant and other immunoadjuvants. The anti-GAP43 antibody of the invention may be purified from antiserum by affinity chromatography using the above polypeptide attached to an appropriate solid support.

Hybridoma which produces the anti-GAP43 antibody of the invention may be prepared by fusing spleen cells prepared from an immunized mouse with, for example, myeloma cells from an animal allogeneic or xenogeneic to the mouse. The spleen cells and the myeloma cells are mixed with a nonionic surfactant for several minutes, and then inoculated, at a low concentration, into a selection medium which supports the growth of the hybridoma, but not the growth of the myeloma cells. For a selection technology, the HAT (hypoxanthine, aminopterin, thymidine) selection is preferably used. Usually, hybridoma colonies are observed after about 1 or 2 weeks. A single colony is selected, and a culture supernatant thereof is tested for a binding activity against the above polypeptide. By repeating cloning by the limiting dilution method, a hybridoma clone which stably produces a large amount of an antibody having high reactivity and specificity is selected. The monoclonal antibody may be isolated from a supernatant of a colony of a cell line derived from a hybridoma clone selected during growth. Further, various technologies for improving a yield, including intraabdominal injection of the hybridoma into an appropriate vertebrate host such as mouse, may be used. The monoclonal antibody may be purified by affinity chromatography using the polypeptide attached to an appropriate solid support.

The term "an antigen binding fragment of an antibody" as used herein refers to a portion of an antibody which participates in antigen binding. The antigen binding site is formed with amino acid residues in the variable (V) region at the N-termini of the heavy (H) chain and the light (L) chain. Examples of the antigen binding fragment include a Fab fragment or F(ab')$_2$ fragment which can be obtained by digesting an intact polyclonal antibody or an intact monoclonal antibody with protease papain or pepsin, respectively. In addition, examples thereof include an Fv fragment including a non-covalent heterodimer of the $V_H$ region and the $V_L$ region containing an antigen binding site retaining substantial antigen recognition ability and binding ability of the native antibody molecule.

In the context of the anti-GAP43 antibody of the invention, a recombinant antibody may be prepared by expression cloning of an antibody gene which involves transformation into a suitable bacterial host or transfection into a suitable mammalian host cell. In the context of the anti-GAP43 antibody of the invention, a chimeric antibody may be a fusion protein in which an antigen binding site of the anti-GAP43 antibody of the invention is supported by a constant domain of an allogeneic or xenogeneic antibody so that a non-phosphorylated specific serine residue and a non-phosphorylated specific threonine residue of GAP43 can be distinguished from a phosphorylated specific serine residue and a phosphorylated specific threonine residue. The specific serine residue and the specific threonine residue may be a serine residue at position 86 (S86), a threonine residue at position 89 (T89), a threonine residue at position 95 (T95), a serine residue at position 96 (S96), a serine residue at position 103 (S103), a serine residue at position 128 (S128), a serine residue at position 142 (S142), a serine residue at position 145 (S145), a threonine residue at position 171 (T171), a threonine residue at position 172 (T172), or a serine residue at position 192 (S192) of mouse GAP43. The chimera antibody includes a single-chain variable region antibody (scFv) which contains an antibody heavy chain variable region (V$_H$) operably connected to an antibody light chain variable region (V$_L$), and a camel heavy chain antibody (HCAb) which is a class of IgG having no light chain and which is produced in camelidae animals (including camel, dromedary, and lama) or a heavy chain variable domain (V$_H$D) thereof. The recombinant antibody can be prepared in a large amount using a gene expression system derived from procaryote and eukaryote.

A process of "preparing the anti-GAP43 antibody of the invention" in the immunological analysis method of the invention includes obtaining the anti-GAP43 antibody of the invention or preparing the anti-GAP43 antibody of the invention. Methods of obtaining the anti-GAP43 antibody of the invention include obtaining the anti-GAP43 antibody of the invention which is already produced, from a specific supplier with or without consideration. The method of preparing the anti-GAP43 antibody of the invention may be carried out by the above-described various methods known to the person skilled in the art.

The process of "preparing a test sample" in the immunological analysis method of the invention includes obtaining a test sample applicable to the immunological analysis method of the invention or preparing a test sample applicable to the immunological analysis method of the invention. Methods of obtaining a test sample include obtaining a pre-prepared test sample from a specific supplier with or without consideration. The method of preparing a test sample may be carried out by collecting from a living body, cell culturing or the like. Examples of the test sample includes, but not limited to, a collected cell, tissue, and organ, a cultured cell, a cell lysate, and a synthetic polypeptide. The test sample generally includes a GAP43 including at least a portion of the amino acid sequence set forth in SEQ ID NO: 13, a mutant or polypeptide thereof, or a fusion protein thereof. The fusion protein may be a fusion protein in which a GAP43 containing at least a portion of the amino acid sequence set forth in SEQ ID NO: 13, a mutant or polypeptide thereof is fused with a tagged protein or a tagged peptide. Examples of the tagged protein include, but not limited to, green fluorescent protein (EGFP), yellow fluorescence protein (EYFP), and cyan fluorescent protein (ECFP). Examples of the tagged peptide include, but not limited to, a His tag, a Myc tag, a HA tag, and a FLAG tag. A GAP43 containing at least a portion of the amino acid sequence set forth in SEQ ID NO: 13, a mutant or polypeptide thereof, and a fusion protein thereof may be phosphorylated. Biological species from which the test sample is originated include, but not limited to, human, monkey, mouse, and rat as long as a non-phosphorylated specific serine residue or a non-phosphorylated specific threonine residue can be distinguished from a phosphorylated specific serine residue or a phosphorylated specific threonine residue by the anti-GAP43 antibody of the invention. The specific serine residue and the specific threonine residue may be a serine residue at position 86 (S86), a threonine residue at position 89 (T89), a threonine residue at position 95 (T95), a serine residue at position 96 (S96), a serine residue at position 103 (S103), a serine residue at position 128 (S128), a serine residue at position 142 (S142), a serine residue at position 145 (S145), a threonine residue at position 171 (T171), a threonine residue at position 172 (T172), or a serine residue at position 192 (S192) of mouse GAP43.

In the immunological analysis method of the invention, the process of "contacting the anti-GAP43 antibody with the test sample" may be carried out using a solid support on which the test sample is immobilized. Various materials or shapes can be used for the solid support as long as the test sample can be immobilized without losing immunogenicity. The solid support may be manufactured from a material, examples of which include, but not limited to, a polymeric material, glass, ceramics, a gel, membrane, natural fiber, silicone, metal, and a composite material thereof. Examples of the solid support include a solid support having a shape suitable for handling in an automated analysis system, such as a multi-well plate, a microtiter plate, a multi-array chip, a sensor chip, or a particle for the latex agglutination method. In the contact process described above, two or more anti-GAP43 antibodies may be used in combination. The immunological analysis method of the invention may comprise a process of contacting an antibody different from the anti-GAP43 antibody of the invention with the test sample. Examples of the different antibody include, but not limited to, a commercially available anti-β-actin antibody and anti-neurofilament antibody.

In the immunological analysis method of the invention, the process of "detecting or quantifying the anti-GAP43 antibody bound to a test sample" may be detected or quantified by labeling the anti-GAP43 antibody bound to a test sample, a second antibody, or the like. The anti-GAP43 antibody may be labeled with a low-molecular ligand such as biotin, an enzyme, a radioactive isotope, a dye, a fluorescent dye, or the like. A secondary antibody against the anti-GAP43 antibody or a biopolymer such as avidin which specifically binds to the above low-molecular ligand such as biotin may be labeled with an enzyme, a radioactive isotope, a dye, a fluorescent dye, or the like. Examples of the enzyme are peroxidase (POD), beta galactosidase (β-Gal), alkaline phosphatase (ALP), and the like. The enzyme is generally used in combination with an appropriate substrate. The detection process may include a process of exposure to an imaging plate, a process of photographing with a CCD camera, or a process of observing under a microscope. The quantification process may comprise a process of creating a calibration curve in which a numerical value converted from the amount of the anti-GAP43 antibody bound to a known concentration or amount of a test sample is plotted, and a process of calculating a concentration or amount of the test sample from the amount of the anti-GAP43 antibody bound to an unknown concentration or amount of the test sample using the calibration curve. In order to create a calibration curve, at least two test samples in a known concentration or amount are sufficient, but three or four are preferred in order to assure quantification precision. The detection or quantification process may include a process of removing the anti-GAP43 antibody not bound to a test sample and other antibodies by washing.

When neural development and/or regeneration are/is evaluated in the immunological analysis method of the invention, the neural development and/or regeneration may be determined as favorable when the amount of the anti-GAP43 antibody bound to a test sample shows a value higher than a reference value. The reference value can be calculated according to statistical analysis well known to the person skilled in the art. The reference value may be defined as a mean value of the amount of the anti-GAP43 antibody bound to a test sample prepared from a specific population.

The population used in this case may be normal test animals or test animals in which the nerve is regenerated. A test animal from the population and a test animal to be evaluated are preferably the same in terms of biological species, age, and sex.

In the immunological analysis method of the invention, the process of "detecting or quantifying the anti-GAP43 antibody bound to a test sample" may be carried out by various approaches known to the person skilled in the art. Examples of the approaches include, but not limited to, the ELISA method, the western blotting method, the surface plasmon resonance method, the latex agglutination method, the immunohistochemical method, and a combination of two or more of these. The surface plasmon resonance (SPR) method refers to an approach in which a specific interaction on a solid support between a molecule immobilized on the solid support and a counterpart molecule for the interaction is measured as a minute change in mass using an optical phenomenon. For example, as a system for carrying out the SPR method, a BIAcore system (BIAcore, GE Healthcare Japan Corporation) can be used. The latex agglutination method refers to an approach in which a degree of a particulate aggregation reaction which depends on the amount of an antibody bound to a particle or nanoparticle such as latex as a solid support is measured as a change in specific turbidity using a spectrophotometer.

A kit for carrying out the immunological analysis method of the invention may include a known concentration or amount of a control sample for creating a calibration curve in addition to the anti-GAP43 antibody of the invention. The control sample may be a GAP43 which includes at least a portion of the amino acid sequence set forth in SEQ ID NO: 13, and in which a specific serine residue or a specific threonine residue is phosphorylated, a mutant or polypeptide thereof, or a fusion protein thereof. The specific serine residue and the specific threonine residue may be a serine residue at position 86 (S86), a threonine residue at position 89 (T89), a threonine residue at position 95 (T95), a serine residue at position 96 (S96), a serine residue at position 103 (S103), a serine residue at position 128 (S128), a serine residue at position 142 (S142), a serine residue at position 145 (S145), a threonine residue at position 171 (T171), a threonine residue at position 172 (T172), or a serine residue at position 192 (S192) of mouse GAP43. The kit for carrying out the immunological analysis method of the invention may further contain a reagent for detecting or quantifying the anti-GAP43 antibody of the invention. Examples of the reagent include those appropriately selected depending on the approach for detecting or quantifying the anti-GAP43 antibody, and can include for example, a buffer solution such as a phosphate buffer as a diluent, and a color-developing agent.

The invention provides an apparatus for immunologically analyzing GAP43 which is configured to be capable of carrying out the above immunological analysis method. The apparatus includes a detection unit such as a light microscope, a fluorescence microscope, an electron microscope, or a CCD camera; a measurement unit such as a spectrophotometer, a spectrophotofluorometer, or a surface plasmon resonance measurement apparatus; a dispenser unit for pouring and/or removing a reagent, a washing liquid, and/or a sample; a robot arm unit for handling a multi-well plate for ELISA and a sensor chip for surface plasmon resonance; a control unit for controlling these; and the like.

Examples of the invention described below are intended for merely illustrative purposes, and should not be construed as limiting the technical scope of the invention. The technical scope of the invention is only limited by the recitation of the claims. Any modification to the invention, for example, an addition, deletion, and substitution to the configuration of the invention may be carried out without deviating from the sprit of the invention.

The following experiments were carried out after approved by the Niigata university animal experiment ethics committee (Approval Number: Niigata University Research No. 44, Date of Approval: Sep. 27, 2006).

Example 1

Production of Anti-GAP43 Antibody

1 Material and Method
1.1 Obtaining Polypeptide

Twelve non-phosphorylated polypeptides and 12 phosphorylated polypeptides were purchased from Sigma Aldrich Japan. The amino acid sequences of the 12 non-phosphorylated polypeptides are listed in SEQ ID Nos: 1 to 12. The 12 phosphorylated polypeptides will be each described below.

The phosphorylated polypeptide No. 1 was a polypeptide which includes the amino acid sequence of 14 amino acid residues set forth in SEQ ID NO: 1, and in which a threonine residue at position 9 is phosphorylated (hereinafter referred to as "GAP43 pT89"). The phosphorylated polypeptide No. 2 was a polypeptide which includes the amino acid sequence of 13 amino acid residues set forth in SEQ ID NO: 2, and in which a serine residue at position 8 is phosphorylated (hereinafter referred to as "GAP43 pS96"). The phosphorylated polypeptide No. 3 was a polypeptide which includes the amino acid sequence of 14 amino acid residues set forth in SEQ ID NO: 3, and in which a threonine residue at position 9 is phosphorylated (hereinafter referred to as "GAP43 pT172"). The phosphorylated polypeptide No. 4 was a polypeptide which includes the amino acid sequence of 13 amino acid residues set forth in SEQ ID NO: 4, and in which a threonine residue at position 8 is phosphorylated (hereinafter referred to as "GAP43 pT172 (#2)"). The phosphorylated polypeptide No. 5 was a polypeptide which includes the amino acid sequence of 13 amino acid residues set forth in SEQ ID NO: 5, and in which a serine residue at position 8 is phosphorylated (hereinafter referred to as "GAP43 pS142"). The phosphorylated polypeptide No. 6 was a polypeptide which includes the amino acid sequence of 14 amino acid residues set forth in SEQ ID NO: 6, and in which a serine residue at position 9 is phosphorylated (hereinafter referred to as "GAP43 pS145"). The phosphorylated polypeptide No. 7 was a polypeptide which includes the amino acid sequence of 14 amino acid residues set forth in SEQ ID NO: 7, and in which a threonine residue at position 8 is phosphorylated (hereinafter referred to as "GAP43 pT171"). The phosphorylated polypeptide No. 8 was a polypeptide which includes the amino acid sequence of 13 amino acid residues set forth in SEQ ID NO: 8, and in which a serine residue at position 8 is phosphorylated (hereinafter referred to as "GAP43 pS86"). The phosphorylated polypeptide No. 9 was a polypeptide which includes the amino acid sequence of 13 amino acid residues set forth in SEQ ID NO: 9, and in which a threonine residue at position 8 is phosphorylated (hereinafter referred to as "GAP43 pT95"). The phosphorylated polypeptide No. 10 was a polypeptide which includes the amino acid sequence of 13 amino acid residues set forth in SEQ ID NO: 10, and in which a serine residue at position 8 is phosphorylated (hereinafter referred to as "GAP43 pS103"). The phosphorylated polypeptide No. 11 was a polypeptide which includes the amino acid sequence of 13 amino acid residues set forth in SEQ ID NO: 11, and in which a serine residue at position 8 is phosphorylated (hereinafter referred to as "GAP43 pS128"). The phosphorylated polypeptide No. 12 was a polypeptide which includes the amino acid sequence of 13 amino acid residues set forth in SEQ ID NO: 12 and in which a serine residue at position 8 is phosphorylated (hereinafter referred to as "GAP43 pS192").

1.2 Production of Antigen

Twelve peptide antigens were produced by a method well known to the person skilled in the art. Briefly, the 12 polypeptide antigens were each bound to keyhole-limpet hemocyanin (KLH) (Catalog Number H7017, Sigma Aldrich Japan) using m-maleimide benzoyl-N-hydroxysakcinimide ester (MBS) (Catalog Number M2786, Sigma Aldrich Japan).

1.3 Preparation of Antiserum

For initial immunization, 200 µg of the peptide antigen was mixed with Freund's complete adjuvant (FCA) (Catalog Number F5881, Sigma Aldrich Japan), and administered to a rabbit. After the initial immunization, 100 µg of each peptide antigen for GAP43 pT89, GAP43 pS96, GAP43 pS145, GAP43 pT171, and GAP43 pT172 was mixed with Freund's incomplete adjuvant (hereinafter referred to as "FIA") (Catalog Number F5506, Sigma Aldrich Japan), and was administered every 7 days. Blood was collected 49 days after the initial immunization to obtain antiserum. After the initial immunization, 100 µg of each peptide antigen for GAP43 pS86, GAP43 pT95, GAP43 pS103, GAP43 pS128, GAP43 pS142, GAP43 pT172 (#2), and GAP43 pS192 was mixed with FIA, and administered every 14 days. Blood was collected 84 days after the initial immunization to obtain antiserum.

1.4 Purification of Anti-GAP43 Antibody

The antiserum was purified by affinity purification according to a method well known to the person skilled in the art. Briefly, the antiserum was desalted with a PD-10 column (Catalog Number 54805, Sigma Aldrich Japan), and was mixed with a support (Sigma Aldrich Japan) to which the phosphorylated polypeptide had been immobilized. It was mixed with a TOYOPEARL AF-Tresyl-6504B support (Catalog Number 14471, Tosoh Corporation) to which the phosphorylated polypeptide had been immobilized. After mixing, a sedimented support was washed with phosphate buffered saline (hereinafter referred to as "PBS"). An antibody was eluted with 0.1 M glycine hydrochloride buffer (pH 2.5), and neutralized with 1M tris-HCL buffer (pH 8.0). The antibody was prepared with a PBS/50% glycerol/15 ppm a ProClin solution, and stored at −20° C. Hereinbelow, anti-GAP43 antibodies against respective peptide antigens for GAP43 pT89, GAP43 pS96, GAP43 pT172, GAP43 pT172 (#2), GAP43 pS142, GAP43 pS145, GAP43 pT171, GAP43 pS86, GAP43 pT95, GAP43 pS103, GAP43 pS128, and GAP43 pS192 refer to the anti-GAP43 pT89 antibody, the anti-GAP43 pS96 antibody, the anti-GAP43 pT172 antibody, the anti-GAP43 pT172 (#2) antibody, the anti-GAP43 pS142 antibody, the anti-GAP43 pS145 antibody, the anti-GAP43 pT171 antibody, the anti-GAP43 pS86 antibody, the anti-GAP43 pT95 antibody, the anti-GAP43 pS103 antibody, the anti-GAP43 pS128 antibody, and the anti-GAP43 pS192 antibody, respectively.

1.5 Evaluation of Specificity of Anti-GAP43 Antibodies Using ELISA Method

The anti-GAP43 antibodies were studied for cross reactivity by the ELISA method. Briefly, the above 12 non-phosphorylated polypeptides and the above 12 phosphorylated polypeptides were each added to a multi-well plate, and immobilized on the plate. After blocking, the above anti-GAP43 antibodies were each added to the plate as primary antibodies. Then, a peroxidase-labeled goat anti-rabbit IgG antibody was added as a secondary antibody. After adding a substrate solution, absorbance (405 nm) was measured using a microplate reader.

1.6 Evaluation of Specificity of Anti-GAP43 Antibodies Using Western Blotting Method Each anti-GAP43 antibody against GAP43 was studied for cross reactivity by the western blotting method. The western blotting method was carried out in accordance with a standard method well known to the person skilled in the art. Briefly, a growth cone portion (2 µg/mL, 50 µL) (hereinafter referred to as "GCP") of a newborn rat forebrain was used. Final concentrations of the anti-GAP43 rabbit antibodies as primary antibodies were each given as follows. The Anti-GAP43 pS86 antibody (0.7 µg/mL), the anti-GAP43 pT89 antibody (0.35 µg/mL), the anti-GAP43 pT95 antibody (0.09 µg/mL), the anti-GAP43 pS96 antibody (0.5 µg/mL), the anti-GAP43 pS103 antibody (0.6 µg/mL), the anti-GAP43 pS128 antibody (1.26 µg/mL), the anti-GAP43 pS142 antibody (1.37 µg/mL), the anti-GAP43 pS145 antibody (0.75 µg/mL), the anti-GAP43 pT171 antibody (0.78 µg/mL), the anti-GAP43 pT172 antibody (0.26 µg/mL), the anti-GAP43 pT172 (#2) antibody (0.37 µg/mL), and the anti-GAP43 pS192 antibody (0.08 µg/mL). A peroxidase-labeled donkey anti-rabbit IgG antibody (Catalog Number NA934, GE Healthcare Japan Corporation) in an amount of 0.156 µg/mL was used as a secondary antibody. Detection was carried out using an ECL Western blotting detection reagent (Catalog Number RPN2108, GE Healthcare Japan Corporation).

2 Results 2.1 Evaluation of Specificity of Anti-GAP43 Antibodies Using ELISA Method The anti-GAP43 pT89 antibody, the anti-GAP43 pS96 antibody, the anti-GAP43 pT172 antibody, the anti-GAP43 pT172 (#2) antibody, the anti-GAP43 pS142 antibody, the anti-GAP43 pS145 antibody, the anti-GAP43 pT171 antibody, the anti-GAP43 pS86 antibody, the anti-GAP43 pT95 antibody, the anti-GAP43 pS103 antibody, the anti-GAP43 pS128 antibody, and the anti-GAP43 pS192 antibody showed cross reactivity against GAP43 pT89, GAP43 pS96, GAP43 pT172, GAP43 pT172 (#2), GAP43 pS142, GAP43 pS145, GAP43 pT171, GAP43 pS86, GAP43 pT95, GAP43 pS103, GAP43 pS128, and GAP43 pS192, respectively, but did not show cross reactivity against the non-phosphorylated polypeptides (data not shown). Therefore, it was shown that all of the above antibodies were capable of clearly distinguishing a non-phosphorylated polypeptide from a phosphorylated polypeptide.

2.2 Evaluation of Specificity of Anti-GAP43 Antibodies Using Western Blotting Method FIG. 1 shows western blot photographs illustrating the results of the cross reaction experiments for anti-GAP43 antibodies against a sample derived from rat growth cone particles (GCP). The anti-GAP43 pS96 antibody, the anti-GAP43 pT172 antibody, the anti-GAP43 pT89 antibody, the anti-GAP43 pS145 antibody, the anti-GAP43 pT171 antibody, the anti-GAP43 pS142 antibody, and the anti-GAP43 pT172 (#2) antibody showed specific cross reactivity against GCP. Further, the anti-GAP43 pS96 antibody, the anti-GAP43 pT172 antibody, and the anti-GAP43 pT172 (#2) antibody showed particularly strong cross reactivity. It should be noted that the anti-GAP43 pS86 antibody, the anti-GAP43 pT95 antibody, the anti-GAP43 pS103 antibody, the anti-GAP43 pS128 antibody, and the anti-GAP43 pS192 antibody did not show specific cross reactivity against GCP (data not shown).

From the experiment results from this Example, it was shown that the anti-GAP43 pS96 antibody, the anti-GAP43 pT172 antibody, the anti-GAP43 pT89 antibody, the anti-GAP43 pS145 antibody, the anti-GAP43 pT171 antibody, the anti-GAP43 pS142 antibody, and the anti-GAP43 pT172 (#2) antibody each showed specific cross reactivity against GCP. Therefore, it was suggested that the above antibodies were capable of distinguishing a GAP43 in which a specific serine residue or a threonine residue is not phosphorylated from a GAP43 in which a specific serine residue or a threonine residue is phosphorylated.

Example 2

Analysis of Properties of Anti-GAP43 pS96 Antibody and Anti-GAP43 pT172 Antibody 1 Material and Method Properties of the anti-GAP43 pS96 antibody and the anti-GAP43 pT172 antibody were analyzed by the western blotting method as described in Example 1. An expression vector containing a polynucleotide encoding green fluorescent protein (maxGFP) or a fusion protein of mouse GAP43 was transfected into COS-7 cells. The fusion protein was (1) a fusion protein of green fluorescent protein (EGFP) and GAP43 (hereinafter referred to as "EGFP-GAP43"), (2) a fusion protein of EGFP and a mutant in which an amino acid residue at position 96 of GAP43 was replaced with an alanine residue (A) from a serine residue (S) (hereinafter referred to as "EGFP-GAP43 S96A"), (3) a fusion protein of EGFP and a mutant in which an amino acid residue at position 96 of GAP43 was replaced with an aspartic acid residue (D) from a serine residue (S) (hereinafter referred to as "EGFP-GAP43 S96D"), (4) a fusion protein of EGFP and a mutant in which an amino acid residue at position 172 of GAP43 was replaced with an alanine residue (A) from a threonine residue (T) (hereinafter referred to as "EGFP-GAP43 T172A"), (5) a fusion protein of EGFP and a mutant in which an amino acid residue at position 172 of GAP43 was replaced with an aspartic acid residue (D) from a threonine residue (T) (hereinafter referred to as "EGFP-GAP43 T172D"), (6) a fusion protein of a flag tag (FLAG) and GAP43 (hereinafter referred to as "FLAG-GAP43"), (7) a fusion protein of FLAG and a mutant in which an amino acid residue at position 96 of GAP43 was replaced with an alanine residue (A) from a serine residue (S) (hereinafter referred to as "FLAG-GAP43 S96A"), (8) a fusion protein of FLAG and a mutant in which an amino acid residue at position 96 of GAP43 was replaced with an aspartic acid residue (D) from a serine residue (S) (hereinafter referred to as "FLAG-GAP43 S96D"), (9) a fusion protein of FLAG and a mutant in which an amino acid residue at position 172 of GAP43 was replaced with an alanine residue (A) from a threonine residue (T) (hereinafter referred to as "FLAG-GAP43 T172A"), or (10) a fusion protein of FLAG and a mutant in which an amino acid residue at position 172 of GAP43 was replaced with an aspartic acid residue (D) from a threonine residue (T) (hereinafter referred to as "FLAG-GAP43 T172D"). A cell lysate containing the maxGFP or the fusion protein was prepared from COS-7 cells transfected with the expression vector. It should be noted that GCP, a cell lysate prepared from PC12D cells which are undifferentiated nerve cells (hereinafter referred to as "PC12D"), a cell lysate prepared from PC12D stimulated with nerve growth factor (NGF) (hereinafter referred to as "PC12D/NGF(+)"), and a cell lysate prepared from non-transfected COS-7 cells (hereinafter referred to as "COS-7") were used as controls. In order to detect expression of EGFP-GAP43 S96A, EGFP-GAP43 S96D, EGFP-GAP43 T172A, and EGFP-GAP43 T172D, a final concentration of 1 μg/mL anti-EGFP monoclonal antibody (Catalog Number M048-3, Medical & Biological Laboratories Co., Ltd.) was used as a primary antibody while a final concentration of 0.156 μg/mL peroxidase-labeled sheep anti-mouse IgG antibody (Catalog Number NA931, GE Healthcare Japan Corporation) was used as a secondary antibody. In order to compare cross reactivity against EGFP-GAP43 S96A, EGFP-GAP43 S96D, EGFP-GAP43 T172A, and EGFP-GAP43 T172D, a commercially available anti-GAP43 monoclonal antibody (Catalog Number G9264, Sigma Aldrich Japan) and the anti-GAP43 antibodies prepared in Example 1 were used as primary antibodies. For a secondary antibody against the anti-GAP43 monoclonal antibody, a peroxidase-labeled sheep anti-mouse IgG antibody (Catalog Number NA931, GE Healthcare Japan Corporation) was used.

2 Results 2.1 Expression of Fusion Proteins

Figure 2:
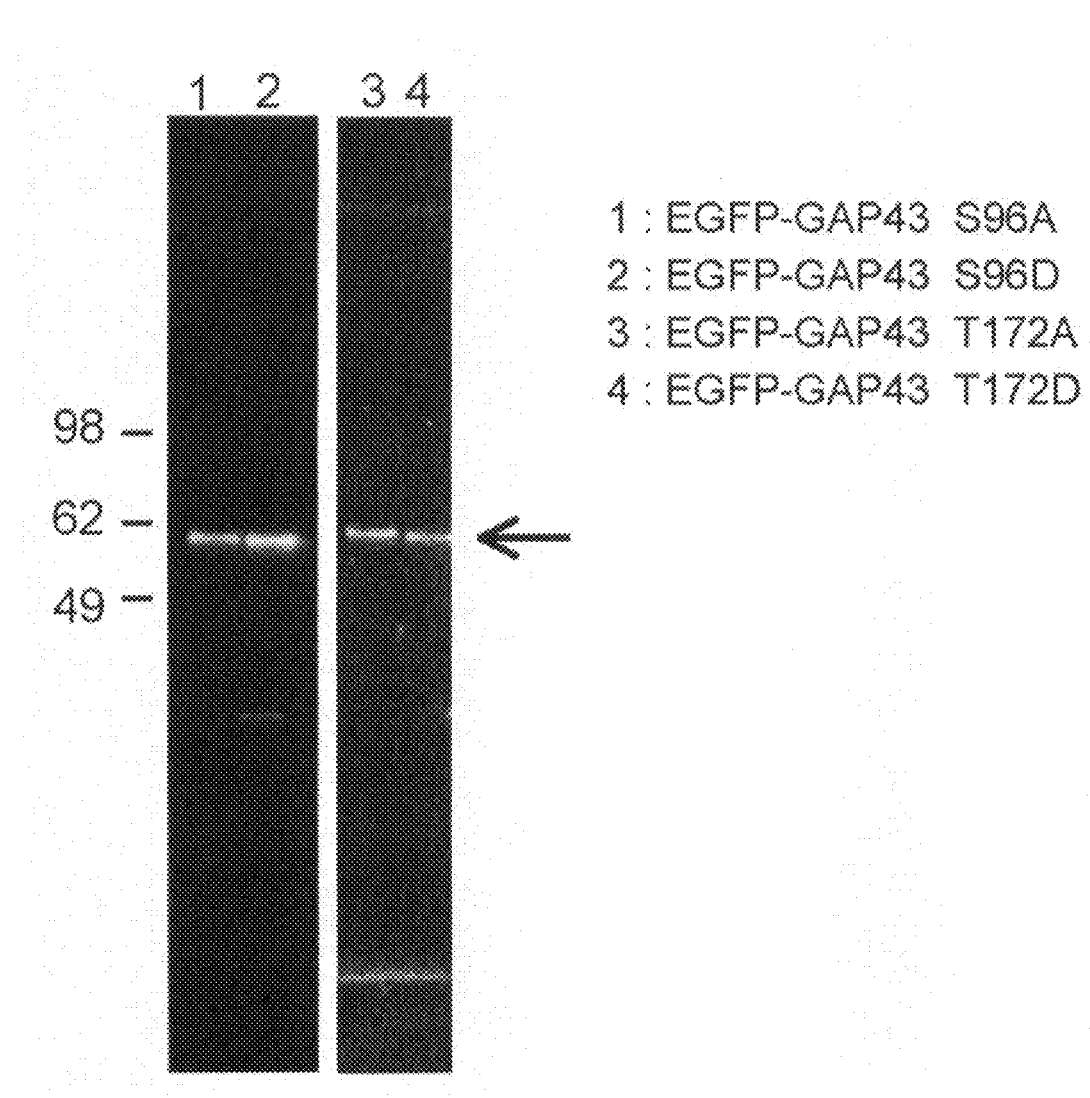
FIG. 2 shows western blot photographs illustrating the results of expression detection experiments for fusion proteins of mouse GAP43.

FIG. 2 shows western blot photographs illustrating the results of the expression detection experiments with the fusion proteins of mouse GAP43. Expressions of EGFP-GAP43 S96A, EGFP-GAP43 S96D, EGFP-GAP43 T172A, and EGFP-GAP43 T172D in COS-7 cells were observed.

2.2 Analysis of Properties of Anti-GAP43 pS96 Antibody

Figure 3:
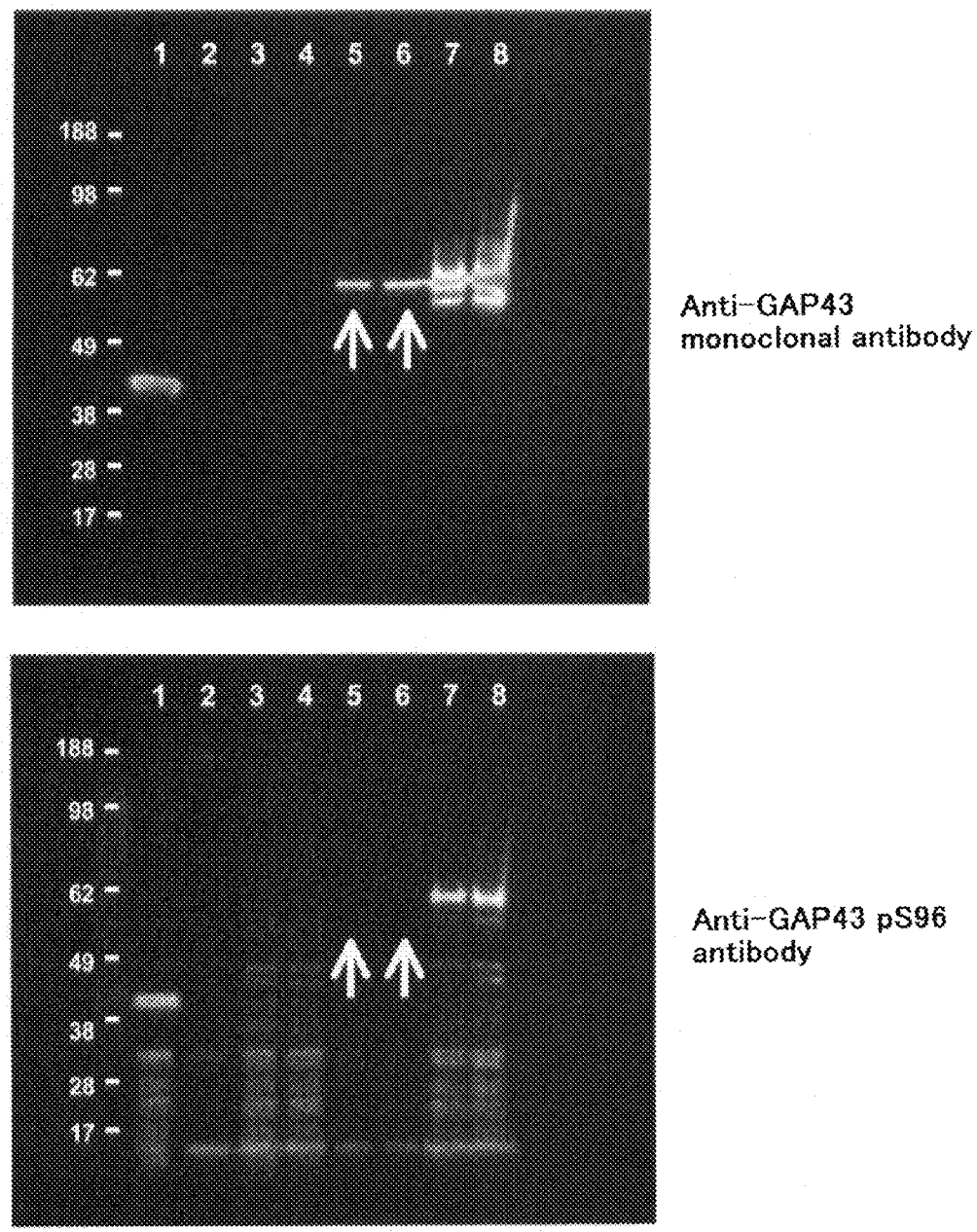
FIG. 3 shows western blot photographs illustrating the results of cross reaction experiment (1) for an anti-GAP43 antibody against various samples.
Figure 4:
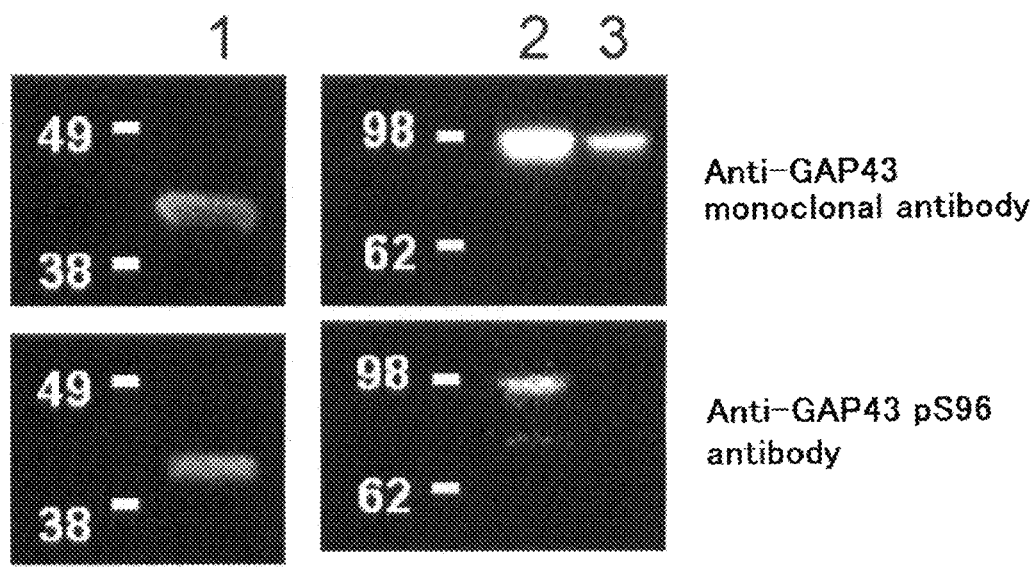
FIG. 4 shows western blot photographs illustrating the results of cross reaction experiment (2) for an anti-GAP43 antibody against various samples.

FIG. 3 shows western blot photographs illustrating the results of the cross reaction experiments for an anti-GAP43 antibody against various samples (1). The anti-GAP43 monoclonal antibody showed cross reactivity against GCP, EGFP-GAP43 S96A, EGFP-GAP43 S96D, EGFP-GAP43 T172A, and EGFP-GAP43 T172D while it did not show cross reactivity against PC12D, COS-7, and maxGFP. Further the anti-GAP43 pS96 antibody showed cross reactivity against GCP, EGFP-GAP43 T172A, and EGFP-GAP43 T172D while it did not show cross reactivity against PC12D, COS-7, maxGFP, EGFP-GAP43 S96A, and EGFP-GAP43 S96D. FIG. 4 shows western blot photographs illustrating the results of the cross reaction experiments for an anti-GAP43 antibody against various samples (2). The anti-GAP43 monoclonal antibody showed cross reactivity against GCP, EGFP-GAP43, and EGFP-GAP43 S96A. The anti-GAP43 pS96 antibody showed cross reactivity against GCP and EGFP-GAP43 while it did not show cross reactivity against EGFP-GAP43 S96A. It should be noted that the anti-GAP43 monoclonal antibody and the anti-GAP43 pS96 antibody showed cross reactivity against PC12D/NGF (+) (data not shown).

2.4 Analysis of Properties of Anti-GAP43 pT172 Antibody

Figure 5:
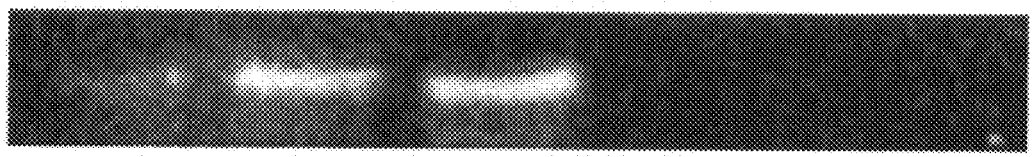
FIG. 5 shows a western blot photograph illustrating the result of cross reaction experiment for the anti-GAP43 pT172 antibody against various samples.

FIG. 5 shows western blot photographs illustrating the results of the cross reaction experiments for the anti-GAP43 pT172 antibody against various samples. The anti-GAP43 pT172 antibody showed cross reactivity against FLAG-GAP43, FLAG-GAP43 S96A, and FLAG-GAP43 S96D while it did not show cross reactivity against FLAG-GAP43 T172A and FLAG-GAP43 T172D.

From the experiment results from this Example, it was shown that the anti-GAP43 monoclonal antibody was not able to distinguish a GAP43 in which a serine residue at position 96 or a threonine residue at position 172 is not phosphorylated from a GAP43 in which a serine residue at position 96 or a threonine residue at position 172 is phosphorylated.

In contrast, it was shown that the anti-GAP43 pS96 antibody was able to distinguish a GAP43 in which a serine residue at position 96 is not phosphorylated from a GAP43 in which a serine residue at position 96 is phosphorylated. Further, it was shown that the anti-GAP43 pT172 antibody was able to distinguish a GAP43 in which a threonine residue at position 172 is not phosphorylated from a GAP43 in which a threonine residue at position 172 is phosphorylated. Furthermore, it was suggested that since the anti-GAP43 pT89 antibody, the anti-GAP43 pS145 antibody, the anti-GAP43 pT171 antibody, the anti-GAP43 pS142 antibody, and the anti-GAP43 pT172 (#2) antibody each showed specific cross reactivity against GCP, they were able to distinguish a GAP43 in which a threonine residue at position 89, a serine residue at position 145, a threonine residue at position 171, a serine residue at position 142, or a threonine residue at position 172 is not phosphorylated from a GAP43 in which a threonine residue at position 89, a serine residue at position 145, a threonine residue at position 171, a serine residue at position 142, or a threonine residue at position 172 is phosphorylated.

Example 3

Immunocytochemical Staining Analysis of Anti-GAP43 Antibodies

1 Material and Method
1.1 Primary Culture of Rat Cerebral Cortex Nerve Cells

Cerebral cortex nerve cells were prepared from the brain of a newborn rat (SD rat, female, Japan SLC, Inc.). Briefly, cerebral cortex nerve cells were treated with a cell dispersion reagent (Accumax®, Innovative Cell Technologies, Inc., Funakoshi Co., Ltd.) and plated on a cover glass coated with 0.05% polyethyleneimine (Catalog Number P3143, Sigma Aldrich Japan). The cover glass was mounted on a culture dish (Catalog Number 353002, Becton, Dickinson and Company Japan), and the cells were cultured at 37° C. and 5% $CO_2$ under the saturated water vapor atmosphere for 3 days using commercially available culture medium (Neurobasal Medium, Catalog Number 21103-049, Invitrogen, Life Technologies Japan Ltd.) containing a B27 supplement (Catalog Number 0050129SA, Invitrogen, Life Technologies Japan Ltd.) and a glutamine-penicillin-streptomycin mixed solution (Catalog Number G6784, Sigma Aldrich Japan).
1.2 Primary Culture of Rat Dorsal Root Ganglion (DRG)

Dorsal root ganglion cells were prepared from rats (SD rats, female and male, 1 day old after birth, Japan SLC, Inc.). Briefly, a portion from the cervical vertebra to the lumbar vertebra was removed, and dorsal root ganglion cells were collected. The dorsal root ganglion cells were plated on a cover glass coated with poly L-lysine (Catalog Number P4832, Sigma Aldrich Japan). The cover glass was mounted on a culture dish (Catalog Number 353002, Becton, Dickinson and Company Japan), and the cells were cultured at 37° C. and 5% $CO_2$ under the saturated water vapor atmosphere for 3 days using commercially available culture medium (Neurobasal Medium, Catalog Number 21103-049, Invitrogen, Life Technologies Japan Ltd.) containing a B27 supplement (Catalog Number 0050129SA, Invitrogen, Life Technologies Japan Ltd.) and a glutamine-penicillin-streptomycin mixed solution (Catalog Number G6784, Sigma Aldrich Japan).
1.3 Immunocytochemical Staining After the culturing, the cells were fixed with Bouin's fixing solution (saturated aqueous picric acid:formalin solution=3:1 <a volume ratio>) for 10 minutes. After washed with PBS, the cells were subjected to a permeabilization treatment with 0.1% Triton X-100/PBS for 10 minutes. Subsequently, immunocytochemical staining was carried out.

For staining, 12 anti-GAP43 antibodies produced in Example 1, a commercially available anti-phosphorylated GAP43 pS41 polyclonal antibody (Catalog Number G8043, Sigma Aldrich Japan), an anti-GAP43 monoclonal antibody, an anti-α-tubulin monoclonal antibody (Catalog Number T9026, Sigma Aldrich Japan) were used as primary antibodies in a 100 to 500 fold dilution. Further, as secondary antibodies, an Alexa 488 fluorescent-labeled goat anti-rabbit IgG antibody (Catalog Number A11034, Invitrogen, Life Technologies Japan Ltd.) and an Alexa 568 fluorescent-labeled goat anti-mouse antibody (Catalog number A11031, Invitrogen, Life Technologies Japan Ltd.) were each used in a 1000-fold dilution. Then, embedding was carried out with a ProLong Gold anti-bleaching reagent (Catalog Number P36930, Invitrogen, Life Technologies Japan Ltd.), and observation was carried out under an inverted fluorescence microscope (Axiovert 200, Carl Zeiss. Inc.).

Figure 6:
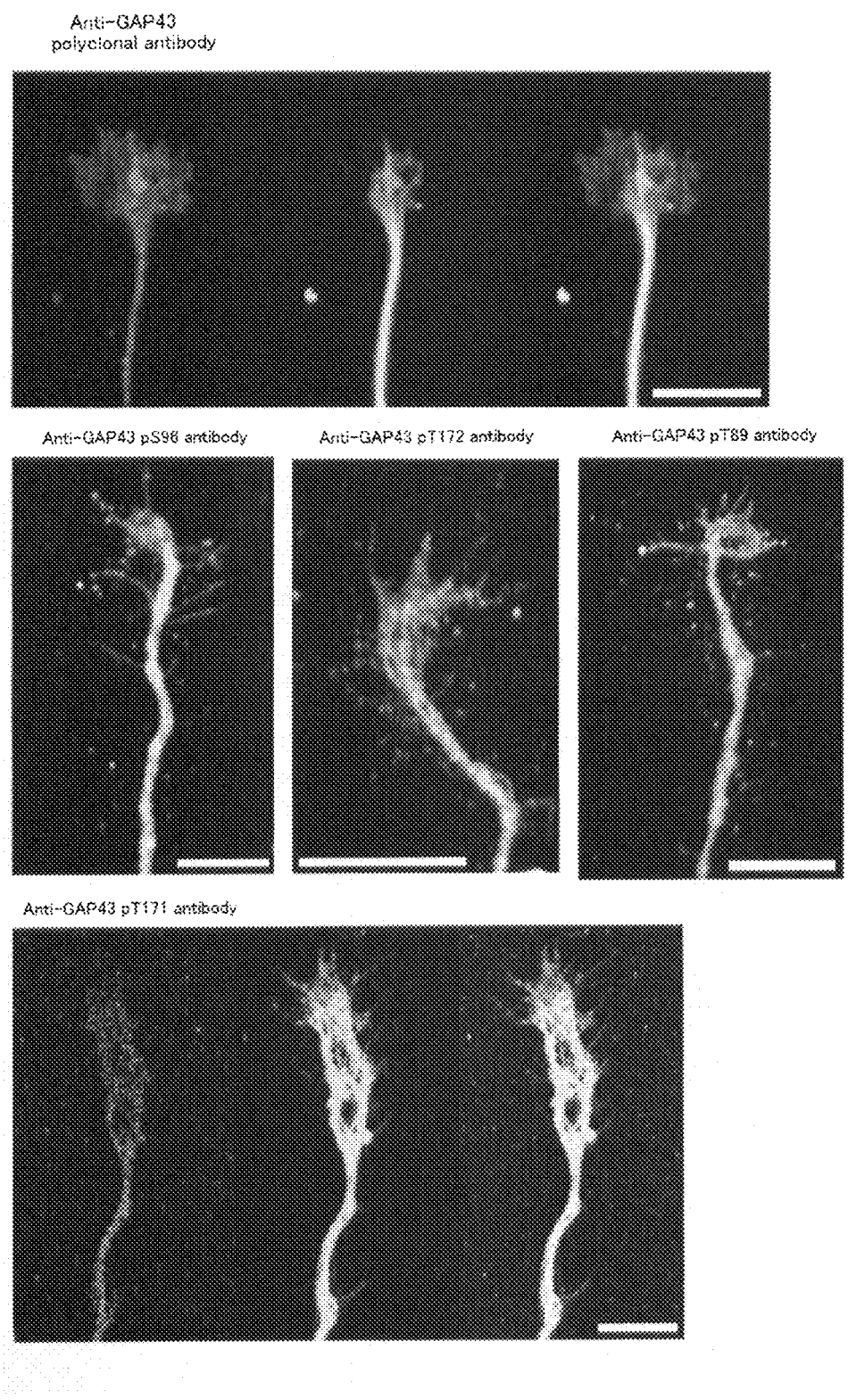
FIG. 6 shows fluorescence microscope photographs of rat cerebral cortex nerve cells immunocytochemically stained with various anti-GAP43 antibodies.
Figure 7:
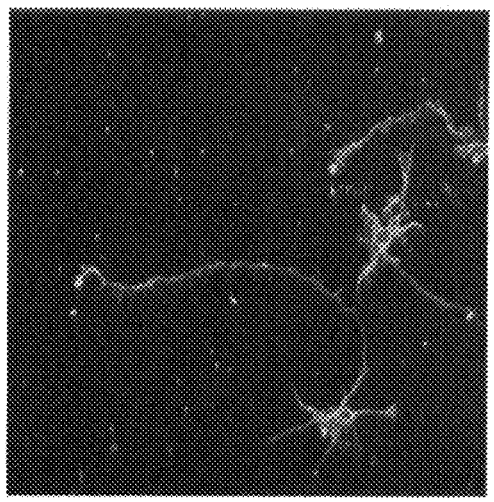
FIG. 7 shows fluorescence microscope photographs of rat cerebral cortex nerve cells immunocytochemically stained with an anti-GAP43 monoclonal antibody and the anti-GAP43 pS96 antibody.
Figure 7:
Figure 7:
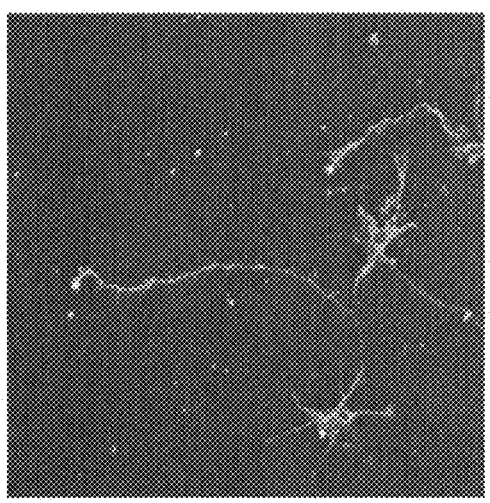
Figure 8:
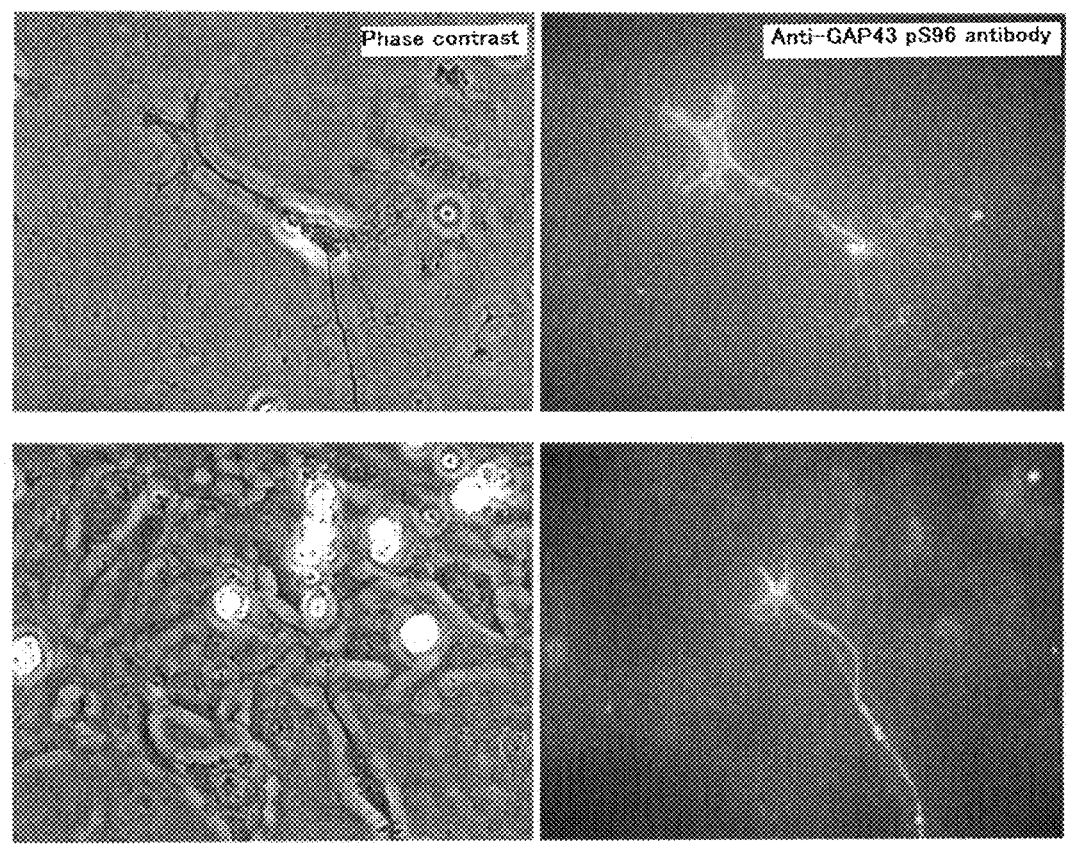
FIG. 8 shows fluorescence microscope photographs of rat dorsal root ganglion nerve cells immunocytochemically stained with the anti-GAP43 pS96 antibody.

Results are shown in FIGS. 6 to 7. In FIG. 6, the left, central, and right images in the upper panels show the anti-GAP43 S41 antibody, an anti-microtubule antibody which recognizes a growth cone and a whole axon (an microtubulin antibody (Catalog Number MAB3408, Nippon Chemi-Con Corporation)), and an merged image thereof, respectively. The left, central, and right images in the lower panels show the anti-GAP43 pT171 antibody, the anti-microtubule antibody, and a merged image thereof, respectively. The term "merged" means superposed double staining images of a respective phosphorylated antibody and another antibody. The upper panels in FIG. 8 show results from the anti-GAP43 pS96 antibody, the lower panels show results from the anti-GAP43 pS171 antibody, in which the left and right images are phase-contrast microscope images and fluorescence microscope photographs, respectively.
2 Results
2.1 Immunocytochemical Staining of Rat Cerebral Cortex Nerve Cells FIG. 6 shows fluorescence microscope photographs of rat cerebral cortex nerve cells immunocytochemically stained with various anti-GAP43 antibodies. The anti-GAP43 pS41 polyclonal antibody and the anti-GAP43 pT171 antibody reacted with a whole nerve cell (see the lower panel in FIG. 6). On the other hand, the anti-GAP43 pS96 antibody, the anti-GAP43 pT172 antibody, and the anti-GAP43 pT89 antibody specifically reacted with a growth cone located at the edge of a nerve cell, especially at the central region.

FIG. 7 shows fluorescence microscope photographs of rat cerebral cortex nerve cells immunocytochemically stained with the anti-GAP43 monoclonal antibody and the anti-GAP43 pS96 antibody. The anti-GAP43 monoclonal antibody reacted with a whole nerve cell including dendrites.
2.2 Immunocytochemical Staining of Rat Dorsal Root Ganglion Cells FIG. 8 shows fluorescence microscope photographs of rat dorsal root ganglion nerve cells immunocytochemically stained with the anti-GAP43 pS96 antibody. The anti-GAP43 pS96 antibody specifically reacted with a growth cone of a ganglion cell at the central region.

In the amino acid sequences of both rat GAP43 and mouse GAP43, positions 41, 89, 96, 171, and 172 are a serine residue, a threonine residue, a serine residue, a threonine residue, and a threonine residue, respectively. Further, the amino acid sequences of SEQ ID Nos: 1 to 12 are conserved in rat GAP43. Therefore, it was predicted that the phosphorylated GAP43 specific antibodies in this Example would react with not only mouse GAP43 but also rat GAP43. This prediction was confirmed by the experimental results from this Example. Further, it was shown that the anti-GAP43 pS96 antibody, the anti-GAP43 pT172 antibody, and the anti-GAP43 pT89 antibody was able to specifically detect a growth cone as compared with the anti-GAP43 monoclonal antibody. In addition, a GAP43 in which a threonine residue at position 89, a serine residue at position 96, or a threonine residue at position 172 is phosphorylated is localized at a growth cone of a nerve cell. Furthermore, a GAP43 in which a threonine residue at position 172 is phosphorylated was localized at a growth cone while a GAP43 in which a threonine residue at position 171 is phosphorylated was present in a whole nerve cell. Therefore, it was suggested that phosphorylation of GAP43 is strictly regulated so that a nerve cell can correctly outgrowth an axon to correctly form a synapse. Particularly for a growth cone, it was suggested that phosphorylation of a threonine residue at position 89, a serine residue at position 96, and a threonine residue at position 172 of GAP43 is more important than phosphorylation of a serine residue at position 41 of GAP43. Further, it was suggested that the anti-GAP43 pT172 (#2) antibody which recognizes the same phosphorylated threonine as the anti-GAP43 pT172 antibody was also able to specifically detect a growth cone.

Example 4

Immunocytochemical Staining Analysis of Anti-GAP43 Antibody

1 Material and Method
1.1 Production of Spinal Injury Model Mouse (Central Nerve Injury Regeneration Model)

A spinal injury treatment was carried out by a method known to the person skilled in the art. Briefly, a mouse (C57BL6J, male, 8 weeks old, Charles River Laboratories Japan, Inc.) was incised at the back under anesthesia to expose the spine. The 8th to 11th thoracic vertebrae (T8 to 11) were excised with an electric drill. Then, using a commercially available instrument (IH Impactor, Precision Systems), a weight (2.5 g) was fallen 3 times from 2 cm above in a vertical direction onto the thoracic vertebra to cause spinal injury. Immunocytochemical staining analysis was carried out at Day 21 after the treatment. A mouse which was not subjected to the spinal injury treatment was used as a control.
1.2 Production of Peripheral Nerve Regeneration Model Mouse (Peripheral Nerve Regeneration Model)

A peripheral nerve regeneration model mouse was prepared by a method well known to the person skilled in the art. Briefly, a mouse (C57BL6J, male, 8 weeks old, Charles River Laboratories Japan, Inc.) was incised at the foot joint under anesthesia, and the musculocutaneous nerve was bypass grafted to the ulnar nerve. Immunocytochemical staining analysis was carried out at Day 7 after the treatment.
1.3 Fetal Brain in Developmental Process Pregnant mice (Slc:ICR, female, 15 days and 12 day of pregnancy, Japan SLC, Inc.) were incised under anesthesia, and fetuses were removed.
1.4 Preparation of Frozen Tissue Section Frozen tissue sections were prepared by a method well known to the person skilled in the art. Briefly, after the spinal injury treatment and dorsal root ganglion injury treatment or after the fetus removal, the above mice were perfusion fixed with 4% paraformaldehyde/PBS (the PFA liquid). The spinal injury region and the dorsal root ganglion injury region were removed, and further fixed with the PFA liquid. The fixed regions were replaced with a sucrose solution, and embedded with a frozen tissue embedding agent (Tissue-tek OCT compound, Catalog Number 4583, Sakura Finetek Japan Co., Ltd.). Sections having a thickness of 10 μm were prepared with a frozen section preparing device (Cryostat, Leica Microsystems GmbH), and mounted on gelatin-coated slide glasses.
1.5. Immunocytochemical staining In the spinal injury model mouse experiments, immunohistochemical staining was carried out in accordance with a method described in Example 3. The anti-GAP43 pS96 antibody, the anti-GAP43 pT172 antibody, the anti-GAP43 monoclonal antibody, and the anti-GAP43 pS41 antibody were used as primary antibodies. Further, an Alexa 488 fluorescent-labeled goat anti-rabbit IgG antibody (Catalog Number A11034, Invitrogen, Life Technologies Japan Ltd.) and an Alexa 568 fluorescent-labeled goat anti-mouse antibody (Catalog number A1131, Invitrogen, Life Technologies Japan Ltd.) were used as secondary antibodies.

In the experiments regarding a fetal brain in the developmental process, the anti-GAP43 pS96 antibody, the anti-GAP43 pT172 antibody, the anti-GAP43 monoclonal antibody, and the anti-GAP43 pS41 antibody were used as primary antibodies. Further, a biotin-labeled horse anti-mouse antibody (Catalog Number BA-2001, VECTOR Laboratories, Inc.) and a biotin-labeled sheep anti-rabbit antibody (Catalog Number BA-1000, VECTOR Laboratories, Inc.) were used as secondary antibodies.

Figure 9:
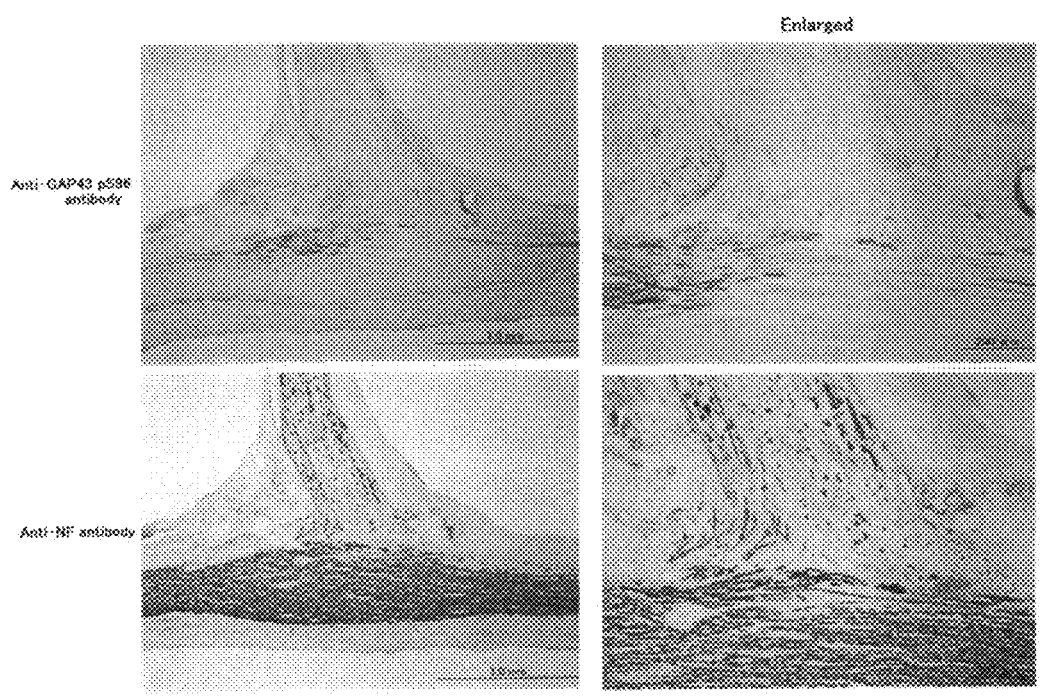
FIG. 9 shows fluorescence microscope photographs of dorsal root ganglion injury regions immunocytochemically stained with the anti-GAP43 pS96 antibody and an anti-neurofilament monoclonal antibody.

In the peripheral nerve regeneration model mouse experiment, immunohistochemical staining was carried out using a commercially available kit (a Vectorstain Elite ABC standard kit, Catalog Number PK6100, Vector Laboratories, Inc., Funakoshi Co., Ltd.) in accordance with a manufacturer's instructions. In the staining, the anti-GAP43 pS96 antibody and the anti-neurofilament (NF) antibody (Catalog Number ab77745, Abcam plc.) were used as primary antibodies. Further, a biotin-labeled sheep anti-mouse antibody (Catalog Number RPN1001 and GE Healthcare Japan Corporation) and a biotin-labeled donkey anti-rabbit antibody (Catalog Number RPN1004, GE Healthcare Japan Corporation) were used as secondary antibodies.
2. Results (Recognition of Regenerated Nerves of Both Peripheral Nerve and Central Nerve)
2.1 Analysis of Peripheral Nerve Regeneration Model Mouse Experiments FIG. 9 shows photographs of a process in which the musculocutaneous nerve bypass-grafted to the ulnar nerve was regenerated from the newly transplanted nerve within the ulnar nerve, which was immunohistochemically analyzed one week after the transplantation. Staining with an anti-NF (neurofilament (intermediate filament)) antibody shows that the nerves are all recognized. Some nerves contain a regenerated nerve from the musculocutaneous nerve, but, only a regenerated nerve can not be captured since the anti-NF antibody recognizes all nerve fibers. The anti-GAP43 pS96 antibody correctly recognized and reacted with only a regenerated nerve among these. The enlarged pictures also show that it reacted with a regenerated nerve from the musculocutaneous nerve in a form found in the course of outgrowth.
2.2 Analysis of Spinal Injury Model Mouse (Central Nerve Injury Regeneration Model)

Figure 10:
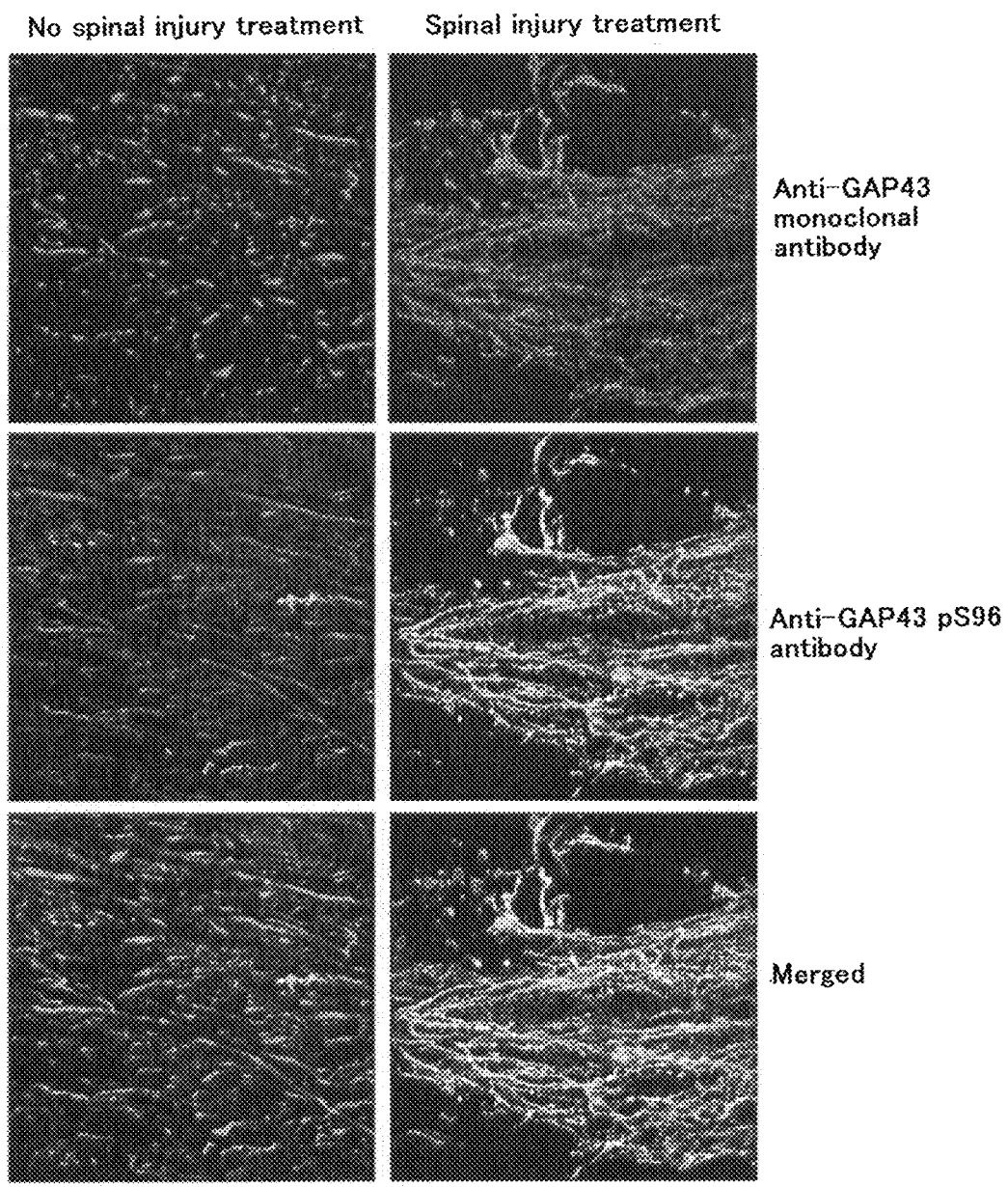
FIG. 10 shows fluorescence microscope photographs of spinal injury regions immunocytochemically stained with the anti-GAP43 pS96 antibody and an anti-GAP43 monoclonal antibody.

FIG. 10 shows fluorescence microscope photographs of the spinal injury regions on Day 21 after the injury which were immunohistochemically stained with the anti-GAP43 pS96 antibody and the anti-GAP43 monoclonal antibody. The anti-GAP43 monoclonal antibody reacted with a nerve cell in the non-injury region and in the injury region. The anti-GAP43 pS96 antibody did not react with a nerve cell in the non-injury region while it reacted with a nerve cell in the injury region.

Figure 11:
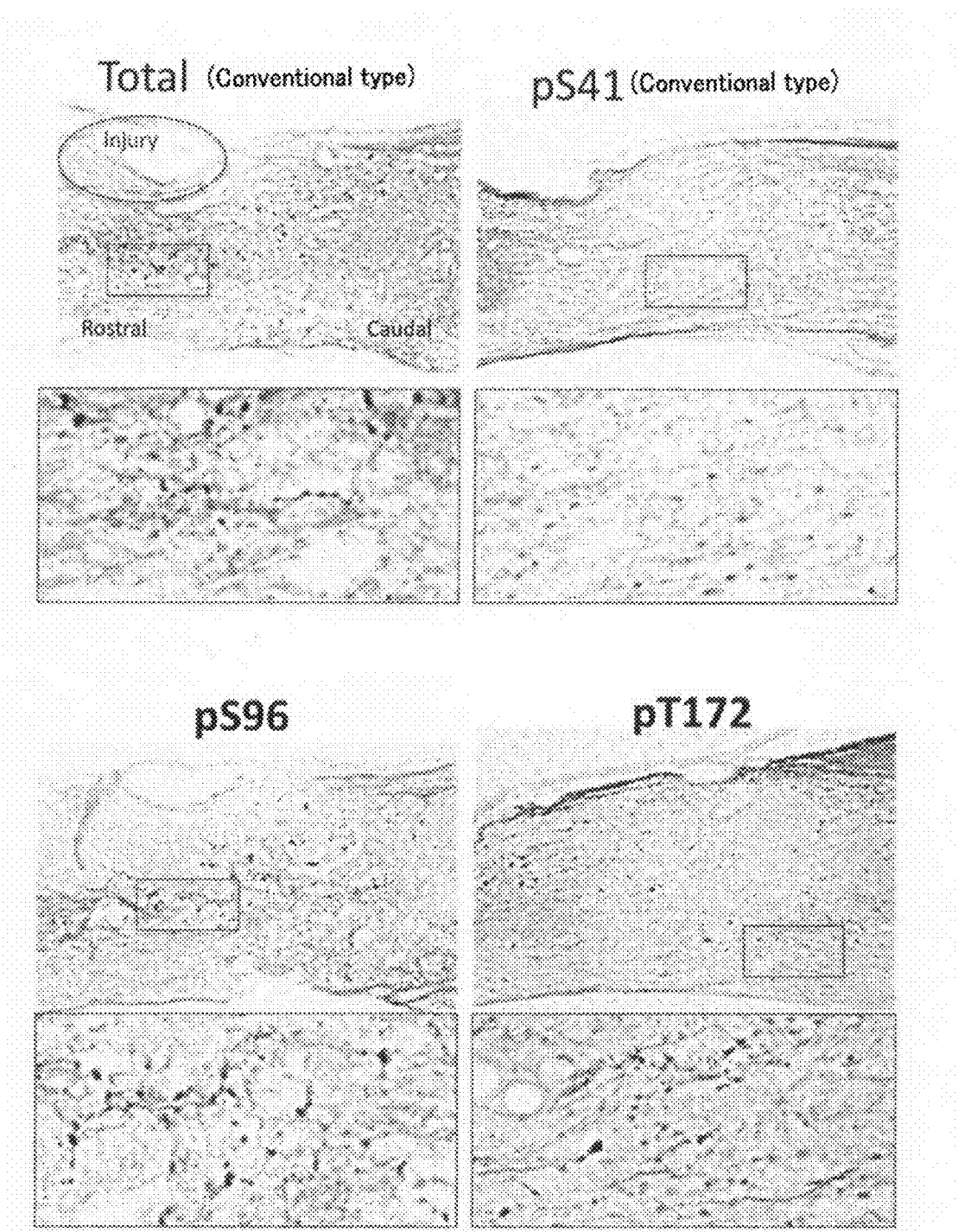
FIG. 11 shows microscope photographs of spinal injury regions at Day 7 after spinal injury which were immunocytochemically stained with the anti-GAP43 pS96 antibody, the anti-GAP43 pT172 antibody, the anti-GAP43 pS41 antibody, and an anti-GAP43 monoclonal antibody.

FIG. 11 shows microscope photographs of the spinal injury regions at Day 7 after the spinal injury which were immunocytochemically stained with the anti-GAP43 pS96 antibody, the anti-GAP43 pT172 antibody, the anti-GAP43 pS41 antibody, and the anti-GAP43 monoclonal antibody. The anti-GAP43 pS41 antibody does not react with a nerve cell in the injury region. The anti-GAP43 pS96 antibody, the anti-GAP43 pT172 antibody reacted with a nerve cell in the injury region.

2.3 Analysis of fetal Brain in Developmental Process

Figure 12:
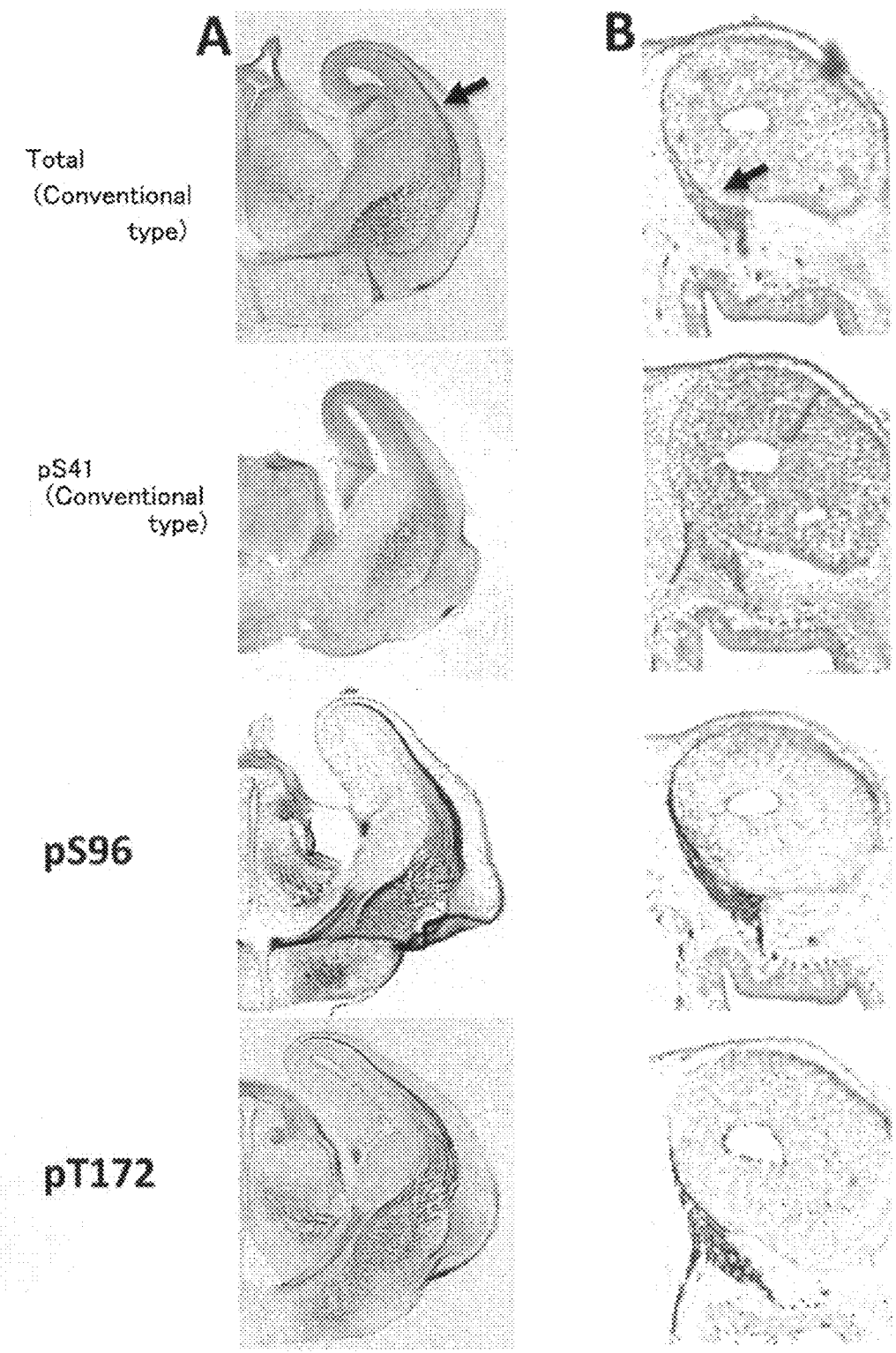
FIG. 12 shows microscope photographs of (A) a thalamus cerebral cortex tract at Embryonic Day 15 and (B) an olfactory nerve at Embryonic Day 15 of a fetal brain in the developmental process which are immunocytochemically stained with the anti-GAP43 pS96 antibody, the anti-GAP43 pT172 antibody, the anti-GAP43 pS41 antibody, and an anti-GAP43 monoclonal antibody.

FIG. 12 shows microscope photographs of (A) the thalamus cerebral cortex tract at Embryonic Day 15 and (B) the olfactory nerve at Embryonic Day 15 of the fetal brain in the developmental process which was immunocytochemically stained with the anti-GAP43 pS96 antibody, the anti-GAP43 pT172 antibody, the anti-GAP43 pS41 antibody, and the anti-GAP43 monoclonal antibody. The anti-GAP43 pS41 antibody does not react with a nerve circuit of A or B. The anti-GAP43 pS96 antibody strongly reacted with a nerve circuit of A and B.

Figure 13:
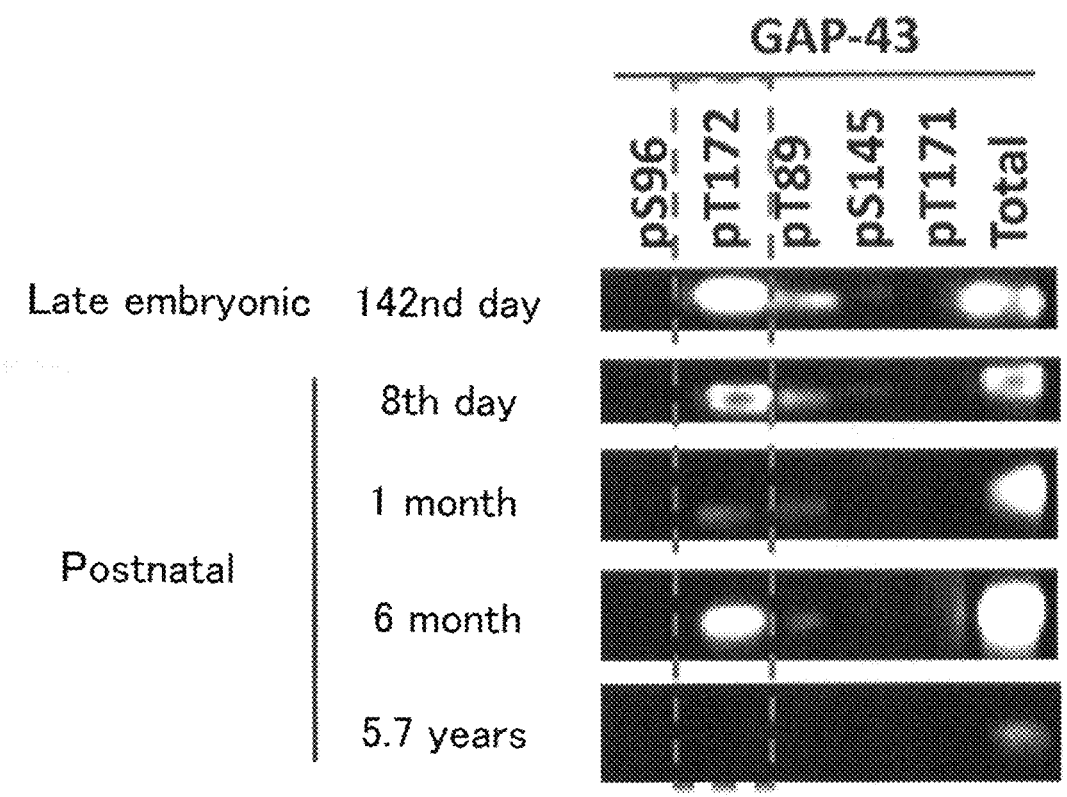
FIG. 13 shows western blot photographs illustrating result of cross reaction experiments for anti-GAP34 antibodies against a rhesus monkey.

2.4 Evaluation of Cross-reactivity of Anti-GAP43 Antibody between Mammals Using Western Blotting Method FIG. 13 shows western blot photographs illustrating the results of cross reaction experiments for anti-GAP34 antibodies against a rhesus monkey. The anti-GAP43 pT172 antibody showed strong cross-reactivity against the visual cortex of the rhesus monkey. It should be noted that the anti-GAP43 pT96 antibody did not show specific cross-reactivity against the rhesus monkey.

From the experimental results in this example, it was shown that the anti-GAP43 pS96 antibody was able to selectively detect nerve cells in the regeneration process of the central nerve and the peripheral nerve while the anti-GAP43 monoclonal antibody was not able to selectively detect the nerve cells. Further, it was suggested that the anti-GAP43 pT89 antibody and the anti-GAP43 pT172 antibody which specifically reacted with a growth cone, and the anti-GAP43 pT 172 (#2) antibody which recognizes the same phosphorylated threonine as the anti-GAP43 pT172 antibody were able to selectively detect nerve cells in the developmental and regeneration processes similarly as the anti-GAP43 pS96 antibody.

CONCLUSION

From the experimental results in these Examples, it was shown that the anti-GAP43 pS96 antibody and the anti-GAP43 pT172 antibody were able to distinguish a GAP43 in which a serine residue at position 96 or a threonine residue at position 172 is not phosphorylated from a GAP43 in which a serine residue at position 96 or a threonine residue at position 172 is phosphorylated. Further, the anti-GAP43 pT89 antibody, the anti-GAP43 pS142 antibody, the anti-GAP43 pS145 antibody, the anti-GAP43 pT171 antibody, and the anti-GAP43 pT172 (#2) antibody each show specific cross-reactivity against GCP, and thus they were able to distinguish a GAP43 in which a threonine residue at position 89, a serine residue at position 142, a serine residue at position 145, a threonine residue at position 171, or a threonine residue at position 172 is not phosphorylated from a GAP43 in which a threonine residue at position 89, a serine residue at position 142, a serine residue at position 145, a threonine residue at position 171, or a threonine residue at position 172 is phosphorylated. Furthermore, it was shown that the anti-GAP43 pT89 antibody, the anti-GAP43 pS96 antibody, and the anti-GAP43 pT172 antibody specifically reacted with a growth cone as compared with the anti-GAP43 monoclonal antibody. Moreover, it was suggested that the anti-GAP43 pT89 antibody, the anti-GAP43 pS96 antibody, the anti-GAP43 pT172 antibody, and the anti-GAP43 pT 172 (#2) antibody were able to detect nerve cells in the developmental and regeneration processes in the central nerve and the peripheral nerve. Therefore, the anti-GAP43 antibody of the invention and the immunological analysis method using the antibody are useful for quantitatively evaluating neural development and/or regeneration.

Japanese Patent Application No. 2011-230577 filed on Oct. 20, 2011, the entire content of which is incorporated herein by reference.

All references, patent applications, and technical specifications cited herein are incorporated herein to a similar extent as if they were specifically and individually stated that the references, patent applications, and technical specifications are individual incorporated herein by reference.

[Sequence List]

The invention claimed is:

1. A method of producing an anti-GAP43 antibody which is capable of distinguishing a non-phosphorylated threonine residue at position 89 (T89) from a phosphorylated threonine residue at position 89 (pT89) of mouse GAP43 set forth in SEQ ID NO: 13, and which is capable of specifically detecting a growth cone, the method comprising:
   injecting a polypeptide comprising at least a part of the mouse GAP43 set forth in SEQ ID NO: 13 to an animal;
   collecting antibodies from the animal;
   subjecting the antibodies to affinity purification; and
   studying the purified antibodies for a cross reactivity thereof and selecting an antibody which shows cross reactivity against a mouse GAP43 having a phosphorylated threonine residue at position 89 (pT89) and which does not show cross reactivity against a non-phosphorylated mouse GAP43 or a mouse GAP43 having a phosphorylated residue other than the threonine residue at position 89.

2. A method of producing an anti-GAP43 antibody which is capable of distinguishing a non-phosphorylated serine residue at position 96 (S96) from a phosphorylated serine residue at position 96 (pS96) of mouse GAP43 set forth in SEQ ID NO: 13, and which is capable of specifically detecting a growth cone, the method comprising:
   injecting a polypeptide comprising at least a part of the mouse GAP43 set forth in SEQ ID NO: 13 to an animal;
   collecting antibodies from the animal;
   subjecting the antibodies to affinity purification; and
   studying the purified antibodies for a cross reactivity thereof and selecting an antibody which shows cross reactivity against a mouse GAP43 having a phosphorylated serine residue at position 96 (pS96) and which does not show cross reactivity against a non-phosphorylated mouse GAP43 or a mouse GAP43 having a phosphorylated residue other than the serine residue at position 96.

3. A method of producing an anti-GAP43 antibody which is capable of distinguishing a non-phosphorylated threonine residue at position 172 (T172) from a phosphorylated threonine residue at position 172 (pT172) of mouse GAP43 set forth in SEQ ID NO: 13, and which is capable of specifically detecting a growth cone, the method comprising:
   injecting a polypeptide comprising at least a part of the mouse GAP43 set forth in SEQ ID NO: 13 to an animal;
   collecting antibodies from the animal;
   subjecting the antibodies to affinity purification; and
   studying the purified antibodies for a cross reactivity thereof and selecting an antibody which shows cross reactivity against a mouse GAP43 having a phosphorylated threonine residue at position 172 (pT172) and which does not show cross reactivity against a non-phosphorylated mouse GAP43 or a mouse GAP43 having a phosphorylated residue other than the threonine residue at position 172.

4. The method of producing an anti-GAP43 antibody according to claim 1, further comprising: selecting an anti-GAP43 antibody which is capable of specifically and significantly immunocytochemically staining and identifying a growth cone or a neural axis in outgrowth of a cultured cell of an animal.

5. The method of producing an anti-GAP43 antibody according to claim 2, further comprising: selecting an anti-GAP43 antibody which is capable of specifically and significantly immunocytochemically staining and identifying a growth cone or a neural axis in outgrowth of a cultured cell of an animal.

6. The method of producing an anti-GAP43 antibody according to claim 3, further comprising: selecting an anti-GAP43 antibody which is capable of specifically and significantly immunocytochemically staining and identifying a growth cone or a neural axis in outgrowth of a cultured cell of an animal.

7. A method of evaluating at least one of neural development and regeneration, the method comprising:
   (1) preparing a test sample and an anti-GAP43 antibody obtained by the method of producing an anti-GAP43 antibody according to claim 1, the anti-GAP43 antibody being capable of distinguishing a non-phosphorylated threonine residue at position 89 (T89) from a phosphorylated threonine residue at position 89 (pT89) of mouse GAP43 set forth in SEQ ID NO: 13, and being capable of specifically detecting a growth cone;
   (2) contacting the anti-GAP43 antibody with the test sample; and
   (3) detecting or quantifying the anti-GAP43 antibody bound to the test sample.

8. A method of evaluating at least one of neural development and regeneration, the method comprising:
   (1) preparing a test sample and an anti-GAP43 antibody obtained by the method of producing an anti-GAP43 antibody according to claim 2, the anti-GAP43 antibody being capable of distinguishing a non-phosphorylated serine residue at position 96 (S96) from a phosphorylated serine residue at position 96 (pS96) of mouse GAP43 set forth in SEQ ID NO: 13, and being capable of specifically detecting a growth cone;
   (2) contacting the anti-GAP43 antibody with the test sample; and
   (3) detecting or quantifying the anti-GAP43 antibody bound to the test sample.

9. A method of evaluating at least one of neural development and regeneration, the method comprising:
   (1) preparing a test sample and an anti-GAP43 antibody obtained by the method of producing an anti-GAP43 antibody according to claim 3, the anti-GAP43 antibody being capable of distinguishing a non-phosphorylated threonine residue at position 172 (T172) from a phosphorylated threonine residue at position 172 (pT172) of mouse GAP43 set forth in SEQ ID NO: 13, and being capable of specifically detecting a growth cone;
   (2) contacting the anti-GAP43 antibody with the test sample; and
   (3) detecting or quantifying the anti-GAP43 antibody bound to the test sample.

10. The immunological analysis method according to claim 7, wherein the detection or quantification of the anti-GAP43 antibody bound to the test sample is carried out using at least one method selected from the group consisting of the ELISA method, the western blotting method, the surface plasmon resonance method, and the latex agglutination method.

11. The immunological analysis method according to claim 8, wherein the detection or quantification of the anti-GAP43 antibody bound to the test sample is carried out using at least one method selected from the group consisting of the ELISA method, the western blotting method, the surface plasmon resonance method, and the latex agglutination method.

12. The immunological analysis method according to claim 9, wherein the detection or quantification of the anti-GAP43 antibody bound to the test sample is carried out using at least one method selected from the group consisting of the ELISA method, the western blotting method, the surface plasmon resonance method, and the latex agglutination method.

13. A method of detecting a growth cone, the method comprising:
   (1) preparing a test sample and an anti-GAP43 antibody obtained by the method of producing an anti-GAP43 antibody according to claim 1;
   (2) contacting the anti-GAP43 antibody with the test sample; and
   (3) detecting or quantifying the anti-GAP43 antibody bound to the test sample.

14. A method of detecting a growth cone, the method comprising:
   (1) preparing a test sample and an anti-GAP43 antibody obtained by the method of producing an anti-GAP43 antibody according to claim 2;
   (2) contacting the anti-GAP43 antibody with the test sample; and
   (3) detecting or quantifying the anti-GAP43 antibody bound to the test sample.

15. A method of detecting a growth cone, the method comprising:
   (1) preparing a test sample and an anti-GAP43 antibody obtained by the method of producing an anti-GAP43 antibody according to claim 3;
   (2) contacting the anti-GAP43 antibody with the test sample; and
   (3) detecting or quantifying the anti-GAP43 antibody bound to the test sample.

* * * * *

SEQUENCE LISTING

```
<160> NUMBER OF SEQ ID NOS: 13

<210> SEQ ID NO 1
<211> LENGTH: 14
<212> TYPE: PRT
<213> ORGANISM: Artificial
<220> FEATURE:
<223> OTHER INFORMATION: GAP43 T89

<400> SEQUENCE: 1

Cys Glu Gly Asp Gly Ser Ala Thr Thr Asp Ala Ala Pro Ala
1               5                   10

<210> SEQ ID NO 2
<211> LENGTH: 13
<212> TYPE: PRT
<213> ORGANISM: Artificial
<220> FEATURE:
```

-continued

<223> OTHER INFORMATION: GAP43 S96

<400> SEQUENCE: 2

Cys Asp Ala Ala Pro Ala Thr Ser Pro Lys Ala Glu Glu
1               5                   10

<210> SEQ ID NO 3
<211> LENGTH: 14
<212> TYPE: PRT
<213> ORGANISM: Artificial
<220> FEATURE:
<223> OTHER INFORMATION: GAP43 T172

<400> SEQUENCE: 3

Cys Val Thr Asp Ala Ala Ala Thr Thr Pro Ala Ala Glu Asp
1               5                   10

<210> SEQ ID NO 4
<211> LENGTH: 13
<212> TYPE: PRT
<213> ORGANISM: Artificial
<220> FEATURE:
<223> OTHER INFORMATION: GAP43 T172 (#2)

<400> SEQUENCE: 4

Cys Thr Asp Ala Ala Ala Thr Thr Pro Ala Ala Glu Asp
1               5                   10

<210> SEQ ID NO 5
<211> LENGTH: 13
<212> TYPE: PRT
<213> ORGANISM: Artificial
<220> FEATURE:
<223> OTHER INFORMATION: GAP43 S142

<400> SEQUENCE: 5

Cys Lys Ala Thr Thr Asp Asn Ser Pro Ser Ser Lys Ala
1               5                   10

<210> SEQ ID NO 6
<211> LENGTH: 14
<212> TYPE: PRT
<213> ORGANISM: Artificial
<220> FEATURE:
<223> OTHER INFORMATION: GAP43 S145

<400> SEQUENCE: 6

Cys Thr Thr Asp Asn Ser Pro Ser Ser Lys Ala Glu Asp Gly
1               5                   10

<210> SEQ ID NO 7
<211> LENGTH: 14
<212> TYPE: PRT
<213> ORGANISM: Artificial
<220> FEATURE:
<223> OTHER INFORMATION: GAP43 T171

<400> SEQUENCE: 7

Cys Val Thr Asp Ala Ala Ala Thr Thr Pro Ala Ala Glu Asp
1               5                   10

<210> SEQ ID NO 8
<211> LENGTH: 13
<212> TYPE: PRT
<213> ORGANISM: Artificial
<220> FEATURE:
<223> OTHER INFORMATION: GAP43 S86

```
<400> SEQUENCE: 8

Cys Lys Lys Glu Gly Asp Gly Ser Ala Thr Thr Asp Ala
1               5                   10

<210> SEQ ID NO 9
<211> LENGTH: 13
<212> TYPE: PRT
<213> ORGANISM: Artificial
<220> FEATURE:
<223> OTHER INFORMATION: GAP43 T95

<400> SEQUENCE: 9

Cys Thr Asp Ala Ala Pro Ala Thr Ser Pro Lys Ala Glu
1               5                   10

<210> SEQ ID NO 10
<211> LENGTH: 13
<212> TYPE: PRT
<213> ORGANISM: Artificial
<220> FEATURE:
<223> OTHER INFORMATION: GAP43 S103

<400> SEQUENCE: 10

Cys Pro Lys Ala Glu Glu Pro Ser Lys Ala Gly Asp Ala
1               5                   10

<210> SEQ ID NO 11
<211> LENGTH: 13
<212> TYPE: PRT
<213> ORGANISM: Artificial
<220> FEATURE:
<223> OTHER INFORMATION: GAP43 S128

<400> SEQUENCE: 11

Cys Ser Glu Glu Lys Ala Gly Ser Ala Glu Thr Glu Ser
1               5                   10

<210> SEQ ID NO 12
<211> LENGTH: 13
<212> TYPE: PRT
<213> ORGANISM: Artificial
<220> FEATURE:
<223> OTHER INFORMATION: GAP43 S192

<400> SEQUENCE: 12

Cys Thr Glu Thr Ala Glu Ser Ser Gln Ala Glu Glu Glu
1               5                   10

<210> SEQ ID NO 13
<211> LENGTH: 227
<212> TYPE: PRT
<213> ORGANISM: Mus musculus
<220> FEATURE:
<221> NAME/KEY: MISC_FEATURE
<223> OTHER INFORMATION: mouse GAP43 amino acid sequence

<400> SEQUENCE: 13

Met Leu Cys Cys Met Arg Arg Thr Lys Gln Val Glu Lys Asn Asp Glu
1               5                   10                  15

Asp Gln Lys Ile Glu Gln Asp Gly Val Lys Pro Glu Asp Lys Ala His
                20                  25                  30

Lys Ala Ala Thr Lys Ile Gln Ala Ser Phe Arg Gly His Ile Thr Arg
            35                  40                  45

Lys Lys Leu Lys Gly Glu Lys Lys Gly Asp Ala Pro Ala Ala Glu Ala
```

-continued

```
                50                  55                  60
Glu Ala Lys Glu Lys Asp Asp Ala Pro Val Ala Asp Gly Val Glu Lys
65                  70                  75                  80

Lys Glu Gly Asp Gly Ser Ala Thr Thr Asp Ala Ala Pro Ala Thr Ser
                85                  90                  95

Pro Lys Ala Glu Glu Pro Ser Lys Ala Gly Asp Ala Pro Ser Glu Glu
                100                 105                 110

Lys Lys Gly Glu Gly Asp Ala Ala Pro Ser Glu Glu Lys Ala Gly Ser
                115                 120                 125

Ala Glu Thr Glu Ser Ala Ala Lys Ala Thr Thr Asp Asn Ser Pro Ser
                130                 135                 140

Ser Lys Ala Glu Asp Gly Pro Ala Lys Glu Glu Pro Lys Gln Ala Asp
145                 150                 155                 160

Val Pro Ala Ala Val Thr Asp Ala Ala Ala Thr Thr Pro Ala Ala Glu
                165                 170                 175

Asp Ala Ala Thr Lys Ala Ala Gln Pro Pro Thr Glu Thr Ala Glu Ser
                180                 185                 190

Ser Gln Ala Glu Glu Glu Lys Asp Ala Val Asp Glu Ala Lys Pro Lys
                195                 200                 205

Glu Ser Ala Arg Gln Asp Glu Gly Lys Glu Asp Pro Glu Ala Asp Gln
210                 215                 220

Glu His Ala
225
```